US008871510B2

(12) United States Patent
Spangrude et al.

(10) Patent No.: US 8,871,510 B2
(45) Date of Patent: Oct. 28, 2014

(54) METHODS FOR GENERATING T LYMPHOCYTES FROM HEMATOPOIETIC STEM CELLS

(75) Inventors: Gerald John Spangrude, Salt Lake City, UT (US); Birgitta H. Mitchell, Salt Lake City, UT (US); Jared Manning, Twin Falls, ID (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/512,988

(22) PCT Filed: Dec. 2, 2010

(86) PCT No.: PCT/US2010/058720
§ 371 (c)(1),
(2), (4) Date: Sep. 6, 2012

(87) PCT Pub. No.: WO2011/068962
PCT Pub. Date: Jun. 9, 2011

(65) Prior Publication Data
US 2013/0005035 A1    Jan. 3, 2013

Related U.S. Application Data

(60) Provisional application No. 61/283,390, filed on Dec. 3, 2009.

(51) Int. Cl.
C12N 5/078    (2010.01)
C12N 5/0783   (2010.01)
C12N 5/0789   (2010.01)

(52) U.S. Cl.
CPC .......... *C12N 5/0636* (2013.01); *C12N 2501/23* (2013.01); *C12N 2502/1394* (2013.01); *C12N 5/0646* (2013.01); *C12N 2501/125* (2013.01); *C12N 2502/99* (2013.01); *C12N 2501/26* (2013.01); *C12N 2501/052* (2013.01); *C12N 2501/42* (2013.01); *C12N 2500/38* (2013.01)
USPC ............ 435/377; 435/372; 435/384; 435/431

(58) Field of Classification Search
CPC combination set(s) only.
See application file for complete search history.

(56) References Cited

U.S. PATENT DOCUMENTS

2004/0171148 A1    9/2004 Schmitt et al.

FOREIGN PATENT DOCUMENTS

| WO | WO-01/32841     | 5/2001 |
| WO | WO-2008/044876  | 4/2008 |
| WO | WO-2008/101272  | 8/2008 |
| WO | WO-2010/051634  | 5/2010 |

OTHER PUBLICATIONS

Alexopoulou, L. et al., "Recognition of double-stranded RNA and activation of NF-κB by Toll-like receptor 3," Nature, 413, (2001), pp. 732-738.

Aliprantis, AO et al., "Cell activation and apoptosis by bacterial lipoproteins through toll-like receptor-2," Science, vol. 285, (Jul. 30, 1999), pp. 736-739.
Altman, J.D. et al., "Phenotypic analysis of antigen-specific T lymphocytes", Science, vol. 274, No. 5284, (Oct. 4, 1996), pp. 94-96 [published erratum appears in Science, 280, (1998), pp. 1821].
Beutler, B., "Toll-like receptors: How they work and what they do," Curr Opin Hematol, 9(1), (Jan. 2002), pp. 2-10.
Dai, Bingbing et al., "In Vitro Differentiation of Adult Bone Marrow Progenitors into Antigen-Specific CD4 Helper T Cells Using Engineered Stromal Cells Expressing a Notch Ligand and a Major Histocompatibility Complex Class II Protein," Stem Cells and Development, vol. 18, No. 2, (2009), pp. 235-245.
Diebold, Sandra S. et al, "Innate Antiviral Responses by Means of TLR7-Mediated Recognition of Single-Stranded RNA," Science, vol. 303, (Mar. 5, 2004), pp. 1529-1531.
Georgescu, Constantin et al., "A gene regulatory network armature for T lymphocyte specification," Proc Natl Acad Sci USA, vol. 105, No. 51, (Dec. 23, 2008), pp. 20100-20105.
Hayashi, F. et al., "The innate immune response to bacterial flagellin is mediated by Toll-like receptor 5," Nature, 410, (Apr. 26, 2001), pp. 1099-1103.
Heil, Florian et al., "Species-Specific Recognition of Single-Stranded RNA via Toll-like Receptor 7 and 8," Science, vol. 303, (Mar. 5, 2004), pp. 1526-1529.
Hemmi, Hiroaki et al., "A Toll-like receptor recognizes bacterial DNA," Nature, vol. 408, (Dec. 7, 2000), pp. 740-745.
Huang, Jiaxue et al., "Propensity of Adult Lymphoid Progenitors to Progress to DN2/3 Stage Thymocytes with Notch Receptor Ligation," J Immunol., 175(8), (Oct. 15, 2005), pp. 4858-4865.
International Preliminary Report on Patentability received in Application No. PCT/US2010/058720 dated Jun. 14, 2012 (9 pages).
International Search Report and Written Opinion of the International Searching Authority in Application No. PCT/US2010/058720 dated Mar. 29, 2011 (15 pages).
La Motte-Mohs, Ross N. et al., "Induction of T-cell development from human cord blood hematopoietic stem cells by Delta-like 1 in vitro," Blood, vol. 105, No. 4, (2005), pp. 1431-1439.
Lopez-Lluch, G. et al., "Cellular redox state and activating protein-1 are involved in ascorbate effect on calcitriol-induced differentiation," Protoplasma, 217(1-3), (2001), pp. 129-136.
Martin, Colin H. et al,. "Differences in lymphocyte developmental potential between human embryonic stem cell and umbilical cord blood-derived hematopoietic progenitor cells," Blood, vol. 112, No. 7, (2008), pp. 2370-2737.
Paulos, Chrystal M. et al., "Adoptive immunotherapy: Good habits instilled at youth have long-term benefits," Immunol Res., vol. 42, Issue 1-3, (Oct. 2008), pp. 182-196.

(Continued)

Primary Examiner — Daniel C Gamett
(74) Attorney, Agent, or Firm — Michael Best & Friedrich LLP

(57) ABSTRACT

This disclosure describes methods for differentiating T cells and NK cells in vitro from hematopoietic stem cells or precursor cells. The technology is directed to methods for the production of selected populations of lymphocytes, such as T cells and NK cells. The availability of such cell populations allows for the complete reconstitution of a depleted, defective or missing lymphocyte population in a patient.

13 Claims, 11 Drawing Sheets

(56) References Cited

OTHER PUBLICATIONS

Poltorak, Alexander et al., "Defective LPS Signaling in C3H/HeJ and C57BL/10ScCr Mice: Mutations in Tlr4 Gene," Science, vol. 282, (Dec. 11, 1998), pp. 2085-2088.

Schmitt, Thomas M. et al., "Induction of T Cell Development from Hematopoietic Progenitor Cells by Delta-like-1 In Vitro," Immunity, vol. 17, (Dec. 2002), pp. 749-756.

Schmitt, Thomas M. et al., "Maintenance of T Cell Specification and Differentiation Requires Recurrent Notch Receptor-Ligand Interactions," J. Exp. Med., vol. 200, No. 4, (Aug. 16, 2004), pp. 469-479.

Schnare, Markus et al., "Recognition of CpG DNA is mediated by signaling pathways dependent on the adaptor protein MyD88," Curr Biol, vol. 10, No. 18, (2000), pp. 1139-1142.

Schwarz, Katrin et al., "Role of Toll-like receptors in constimulating cytotoxic T cell responses," European Journal of Immunology, vol. 33, Issue 6, (Jun. 2003), pp. 1465-1470.

Siddiq, Ambreena et al., "Prolyl 4-hydroxylase activity-responsive transcription factors: From hydroxylation to gene expression and neuroprotection," Front Biosci., 13, (2008), pp. 2875-2887.

Simmons, Jana M. et al., "FeII/α-ketoglutarate hydroxylases involved in nucleobase, nucleoside, nucleotide, and chromatin metabolism," Dalton Transactions, Issue 38, (2008), pp. 5132-5142.

Underhill, D.M. et al., "The Toll-like receptor 2 is recruited to macrophage phagosomes and discriminates between pathogens," Nature, 401, (1999), pp. 811-815.

Van Coppernolle, Stefanie et al., "Functionally Mature CD4 and CD8 TCRαβ Cells Are Generated in OP9-DL1 Cultures from Human CD34+ Hematopoietic Cells," The Journal of Immunology, vol. 183, No. 8, (2009), pp. 4859-4870.

Wang, Hongfang et al., "Distinct roles of IL-7 and stem cell factor in the OP9-DL1 T cell differentiation culture system," Exp. Hematol., vol. 34, No. 12, (Dec. 2006), pp. 1730-1740.

Zakrzewski, Johannes L. et al., "Adoptive transfer of T-cell precursors enhances T-cell reconstitution after allogeneic hematopoietic stem cell transplantation," Nature Medicine, 12, (2006), pp. 1039-1047.

METHODS FOR GENERATING T LYMPHOCYTES FROM HEMATOPOIETIC STEM CELLS

CROSS REFERENCE TO RELATED APPLICATIONS

This application is a U.S. National Stage of PCT/US2010/058720, filed Dec. 2, 2010, which claims priority to U.S. Provisional Application No. 61/283,390, filed Dec. 3, 2009. The entire contents of the foregoing applications are hereby incorporated by reference in their entirety.

STATEMENT OF GOVERNMENT RIGHTS

This invention was made with government support under AI086238 awarded by National Institutes of Health. The government has certain rights in this invention.

TECHNICAL FIELD

This disclosure relates generally to compositions and methods for the in vitro production of T lymphocyte cells from hematopoietic stem cells or precursor cells.

BACKGROUND

The following description is provided to assist the understanding of the reader. None of the information provided or references cited is admitted to be prior art to the present invention.

Lymphocytes are derived from pluripotent stem cells that originate in the fetal liver and bone marrow. T lymphocyte differentiation normally occurs via a series of discrete developmental stages involving an initial primitive progenitor cell without lymphocyte specific cell surface markers ($CD34^+$ $CD3^-CD4^-CD8^-$), followed by acquisition of lymphocyte specific markers and loss of CD34 ($CD34^-CD3^+CD4^+$ $CD8^+$), followed by differentiation into mature $CD3^+$ T cells expressing either CD4 or CD8 ($CD3^+CD4^+CD8^-$ or $CD3^+$ $CD4^-CD8^+$). Hematopoietic stem cells that are self renewing and pluripotent constitute approximately 1% of low density nucleated bone marrow cells. These cells express a high level of CD34 antigen on their surface, and as these pluripotent cells develop and commit to either the lymphoid, monomyeloid or erythroid cell series, the level of CD34 decreases.

T and NK cells are key regulators in the defense against infections and malignancies and play a direct causative role in autoimmune diseases and graft-versus-host disease. T cells recognize antigenic determinants through a surface receptor called the T cell receptor (TCR). Although similar in function to surface bound immunoglobin, T cell receptors are not secreted. T cells mediate their prime immunological function through direct contact with infected host cells. These infected cells cooperate by displaying (presenting) antigenic fragments of foreign proteins on their surface as a means of signaling to T cells that they are infected. While T cells recognize antigens presented on all host cells, T cells are first activated to recognize these antigens by specialized antigen-presenting cells such as dendritic cells, B cells and macrophages. Antigen-presenting cells also express co-stimulatory molecules on their surfaces which are required for full T cell activation. Together with macrophages, T cells are the main component of the cell-mediated immune response and, through the release of soluble factors, are required for virtually all aspects of the immune response. In addition to the T cell receptor, T cells are characterized by two major T cell-specific surface markers, CD4 and CD8, which define functionally distinct T cell populations. CD4 T cells, called T helper cells, are activated through interaction with antigen-presenting cells and function primarily to activate CD8 T cells, also known as cytotoxic or killer T cells (CTL). CTLs are the main effector T cell mediating the destruction of infected host cells and only recognize foreign antigens that are bound to specialized molecules found on virtually all cells. Thus, most infected cells of the body may serve as CTL targets. Target cells are killed by factors released from CTLs that cause rapid target cell lysis or through the induction of a highly ordered program of events leading to cell death. In addition to activating CTLs, CD4 helper cells also regulate B cell activation through the release of soluble factors. Like B cells, most resting virgin T cells are short-lived unless activated to proliferate and generate both effector and memory T cells.

Natural killer cells do not require presentation of foreign or tumor-derived antigens on target cells to direct their cytotoxic action. NK cells possess a spontaneous cytotoxicity against a range of virally-infected and tumor cells that can be broadened following exposure to IL-2. Such cells are then called lymphokine-activated killer (LAK) cells. NK cells also bind antibody-coated cells and mediate a form of cell killing called antibody-dependent cell-mediated cytotoxicity. However, NK cytotoxicity is specifically inhibited by markers carried by most normal host cells. NK cells also produce a number of growth factors with wide ranging immunological and hematopoietic activity.

Mature T lymphocytes can be expanded and manipulated, and this strategy forms the basis of most current approaches to immunotherapy. In contrast, the developmental aspects of T and B lymphocyte populations have not fully been integrated into the design of immunotherapeutic interventions, due in part to the lack of robust culture models that support the differentiation of T and B cells from uncommitted stem and progenitor cells.

SUMMARY

This disclosure describes methods for differentiating T cells in vitro from hematopoietic stem cells or progenitor cells. The technology is also directed to methods for the production of selected populations of lymphocytes, such as T cells and NK cells. The availability of such cell populations allows for the complete reconstitution of a depleted, defective or missing lymphocyte population in a patient.

In one aspect, the disclosure describes a method for differentiating mammalian T cells in vitro, the method comprising: culturing precursor cells in a first culture medium for a sufficient time to produce progenitor T cells; transferring the progenitor T cells to a second culture medium, wherein the second culture medium lacks nucleotides; and culturing the progenitor T cells in the second culture medium for a sufficient time to produce differentiated T cells from the progenitor T cells.

In one embodiment, the first culture medium comprises minimal essential medium (MEM) as the basal culture medium. In another embodiment, the first culture medium comprises Iscove's Modified Dulbecco's Medium (IMDM) as the basal culture medium. In one embodiment, the second culture medium comprises alpha modification MEM (αMEM) as the basal culture medium.

In one embodiment, the first culture medium comprises a feeder layer of OP9-DL1 cells. In one embodiment, the cells are cultured in the first culture medium for less than about 21 days, less than about 30 days, less than about 45 days, or less than about 60 days.

In one embodiment, the progenitor T cells are cultured in the second culture medium for at least 7 days, at least 10 days, at least 12 days, at least 14 days, at least 21 days, or at least 30 days to produce differentiated T cells from the progenitor T cells.

In one embodiment, the first culture medium, the second culture medium, or both the first culture medium and the second culture medium comprises ascorbate. In one embodiment, the ascorbate is phosphoascorbate. In one embodiment, the ascorbate is present in an effective amount to preferentially differentiate T cells over NK cells. In one embodiment, the amount of ascorbate in the first culture medium, the second culture medium, or both the first culture medium and the second culture medium is from about 10-1000 µg/mL. In one embodiment, the amount of ascorbate in the first culture medium, the second culture medium, or both the first culture medium and the second culture medium is about 100 µg/mL.

In one embodiment, the first culture medium comprises IL-7, Flt3 ligand, or both IL-7 and Flt3 ligand. In one embodiment, the amount of IL-7 in the first culture medium is from about 1-10 ng/mL. In one embodiment, the amount of IL-7 in the first culture medium is about 5 ng/mL. In one embodiment, the amount of Flt3 ligand in the first culture medium is from about 1-10 ng/mL. In one embodiment, the amount of Flt3 ligand in the first culture medium is about 5 ng/mL.

In one embodiment, the precursor cells express CD34. In one embodiment, the precursor cells are bone marrow cells, embryonic stem cells, induced pluripotent stem cells, fetal liver cells, umbilical cord blood cells or peripheral blood cells. In one embodiment, the bone marrow cells include hematopoietic stem cells, hematopoietic progenitor cells or both hematopoietic stem cells and hematopoietic progenitor cells.

In another aspect, the disclosure generally describes a method of preferentially differentiating T cells over NK cells in vitro, the method comprising culturing progenitor cells in a culture medium comprising ascorbic acid for a sufficient time to produce differentiated T cells from the progenitor cells, while suppressing the differentiation of NK cells. In one embodiment, the medium lacks TLR ligands.

In one embodiment, the ascorbate is phosphoascorbate. In one embodiment, the ascorbate is present in an effective amount to preferentially differentiate T cells over NK cells. In one embodiment, the amount of ascorbate in the culture medium is from about 10-1000 µg/mL.

In another aspect, the disclosure describes a method for differentiating NK cells in in vitro cultures the method comprising culturing progenitor cells in a culture medium comprising one or more TLR ligands for a sufficient time to produce differentiated NK cells from the progenitor cells, while suppressing the differentiation of T cells.

In one embodiment, the TLR ligand is selected from the group consisting of: Pam3CSK4 (a TLR1/2 agonist), LPS (a TLR4 agonist), and flagellin (a TLR5 agonist). In one embodiment, the amount of TLR ligand in the culture medium is from about 10 to 1000 ng/ml.

In one embodiment, the culture medium further comprises IL-7, Flt3 ligand, and stem cell factor (SCF). In one embodiment, the amount of IL-7 in the culture medium is from about 1-10 ng/mL. In one embodiment, the amount of Flt3 ligand in the culture medium is from about 1-10 ng/mL. In one embodiment, the amount of SCF in the culture medium is from about 10 to about 1000 ng/mL.

BRIEF DESCRIPTION OF THE FIGURES

FIG. 1A shows the influence of cytokines on cellular expansion. The combination of Flt3L and IL-7 promotes $10^5$-fold expansion over 26 days, while addition of stem cell factor (SCF) enhances this by 5-fold. FIG. 1B shows the influence of heat-decomposed L-glutamine ($\Delta$Q) or ammonium ion ($NH_4Cl$) on expansion and differentiation of the T lineage. Growth is similar in all conditions until day 15 of culture, when the cultures containing $\Delta$Q and ammonium ion cease to expand. The growth inhibition is mainly due to the failure of selection by TCR signaling, as shown by the failure of $CD4^+CD8^+$ double positive (DP) cells to survive and expand.

FIG. 2A, IMDM medium, day 14; FIG. 2B, MEM medium, day 14; FIG. 2C, αMEM medium lacking nucleosides, day 14; FIG. 2D, MEM medium, day 24; FIG. 2E, a switch culture at day 24 that was initiated in MEM and switched to αMEM medium lacking nucleosides at day 14.

FIG. 4A. Cultures initiated in IMDM were maintained in the same conditions (left panel) or switched into αMEM after 14 days (right panel). After 31 days of culture, cultures were evaluated for T cell maturation based on cell surface expression of the two types of T cell receptor (TCR), TCRαδ and TCRαβ. These receptors were expressed in association with CD3 (not shown). The switch into αMEM clearly promoted maturation of αβ T cells, as indicated by the increase in TCRαβ and the decrease in TCRαδ expression. FIG. 4B. The CD4/CD8 double positive (DP) phenotype indicates T cell development. The two panels represent analysis of a culture initiated in MEM and switched to αMEM after 14 days. After 31 days of culture, CD4 and CD8 expression were evaluated on the total viable cell population in the culture (left panel) or on those cells expressing TCRαβ, indicating successful T cell development (right panel). Consistent with previous results using fetal liver progenitor cells, CD8 cells are preferentially expanded compared to CD4 cells in this culture system.

DETAILED DESCRIPTION

Figure 1:
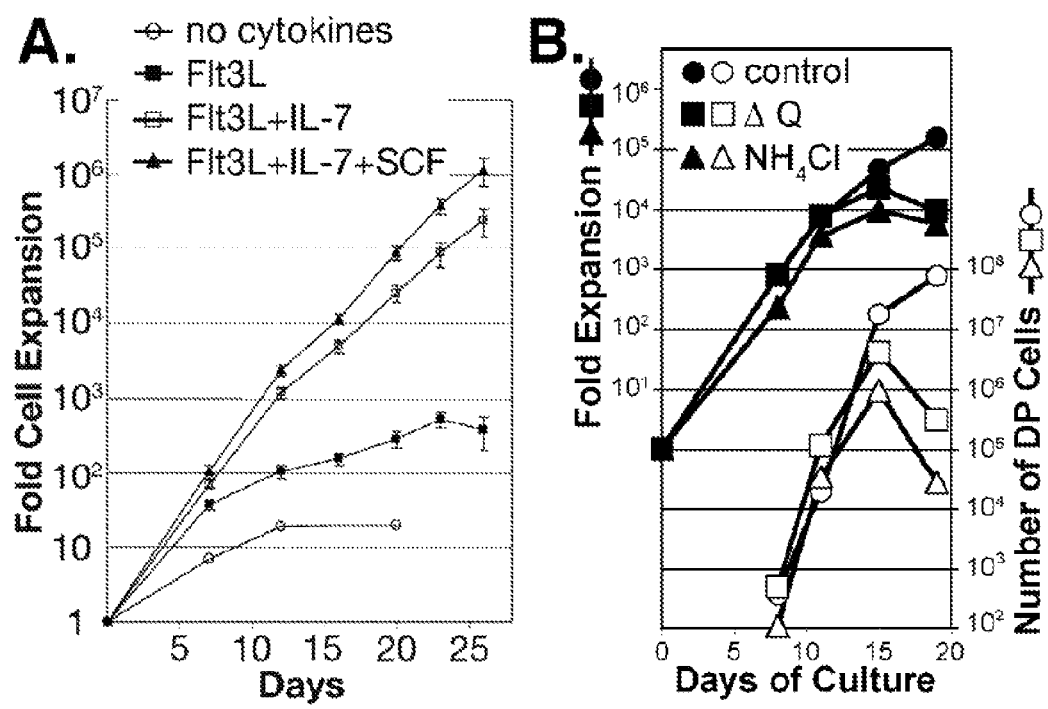
FIG. 1 shows growth kinetics of mouse bone marrow-derived progenitor cells in OP9-DL1 cultures.

The present technology overcomes the problems and disadvantages associated with current strategies and provides new methods for the production of selected populations of lymphocytes. In particular, the present technology generally provides methods for the ex vivo expansion of T cells and NK cells from hematopoietic stem cells or progenitor cells. The methods produce human T cells or NK cells in sufficient amounts for therapeutic use in treating diseases. Accordingly, various aspects of the technology provide culture components and conditions that allow one to culture T cells or NK cells. Cultured human T cells and NK cells are useful, alone or in combination with other therapies, for treating patients suffering from autoimmune disease, graft versus host disease, transplant rejection, an immune-related inflammatory disease, or for promoting transplant tolerance in a host who is to receive a bone marrow, solid organ, or other transplants.

Unless defined otherwise, all technical and scientific terms used herein generally have the same meaning as commonly understood by one of ordinary skill in the art to which this invention belongs. As used in this specification and the appended claims, the singular forms "a", "an", and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

The term "alloantigen" refers to an antigen that differs from an antigen expressed by the recipient. Specifically, an alloantigen is a MHC polymorphism between a host individual and a donor individual of the same species, or between two populations of cells. In the context of a tissue graft or transplant, alloantigens are the nonself MHC expressed by the cells of allografted tissue that can induce an intense immune response in the recipient host and which is aimed at eliminating the transplanted cells. The immune reaction is the result of the host immune cells recognizing the alloantigenic cells or tissue as originating from a nonself source. If an alloantigen is presented to a member of the same species that does not have the alloantigen, it will be recognized as foreign and induce an immune response.

The term "allogeneic" refers to two or more individuals, cells, tissues, or other biological materials that differ at the MHC. Host rejection of grafted tissues from unrelated donors usually results from T-cell responses to allogeneic MHC molecules expressed by the grafted tissues. As used herein, a B cell and a T cell are allogeneic when they differ at the MHC as a result of originating from different individuals. In some contexts, these individuals are a transplant host and donor.

The term "allograft" refers to a graft of cells or tissue from a donor transplanted to a genetically dissimilar recipient, or host, of the same species.

The term "allospecific" refers to being reactive to, identifying, or binding cells or other biological components from genetically disparate individuals within the same species. Allospecific T cells can have effector or regulatory functions, and the relative proportions of the two populations activated following alloantigen presentation is one of the factors that determine the clinical outcome of a tissue graft or transplant, namely, graft rejection or persistence.

The term "anergic" refers to a state of being nonresponsive to an antigen. T cells and B cells are said to be anergic when they cannot respond to their specific antigen under optimal conditions of stimulation. Anergic Treg cells do not mount an immune response, but suppress the response of other effector T cells.

The term "antibody" refers to an immunoglobulin protein that binds specifically to a particular substance, which is called an antigen. Each antibody molecule has a unique structure that enables it to bind specifically to its corresponding antigen, but all antibodies have the same general gross structure.

The term "antigen" refers to any molecule that can bind specifically to an antibody. Antigens typically provoke an immune response in an individual, and this immune response may involve either antibody production or the activation of specific immunologically competent cells, or both. The skilled artisan will understand that any macromolecule, including virtually all proteins or peptides, can serve as an antigen.

The term "antigen presenting cell" (APC) refers to a cell that can process antigens and display antigen peptide fragments on the cell surface together with molecules required for T-cell activation. The main antigen-presenting cells for T cells are dendritic cells, macrophages, and B cells.

The term "autoimmune disease" refers to a condition that results from an adaptive immune response directed at an individual's own cells and tissues expressing self antigens. Autoimmunity can also be described as a loss of self-tolerance. The resulting immune response against self tissues and cells can lead to various acute and chronic disease states as a result of injury to vital organs and tissues. Examples of autoimmune diseases include, but are not limited to, Addison's disease, alopecia greata, ankylosing spondylitis, autoimmune hepatitis, autoimmune parotitis, Crohn's disease, type I diabetes, dystrophic epidermolysis bullosa, epididymitis, glomerulonephritis, Graves's disease, Guillain-Barre syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

The term "autologous" refers to any material derived from the same individual to which it is later to be re-introduced into the same individual.

The term "B cell," or "B lymphocyte," refers to one of the two major types of lymphocytes. Each B cell expresses a particular antigen receptor on its cell surface. On activation by an antigen, B cells differentiate into cells producing antibody molecules of the same antigen specificity as this receptor.

The term "culture medium", refers to a chemical composition that supports the growth and/or differentiation of a cell, suitably of a mammalian cell. Typical culture media include suitable nutrients (e.g. sugars, amino acids, proteins, and the like) to support the growth and/or differentiation of a cell. Media for the culture of mammalian cells are well known to those of skill in the art and include, but are not limited to Medium 199, Eagle's Basal Medium (BME), Eagle's Minimum Essential Medium (MEM), alpha modification MEM (αMEM), Minimum Essential Medium with Non-Essential Amino Acids (MEM/NEAA), Dulbecco's Modification of Eagle's Medium (DMEM), McCoy's 5A, Rosewell Park Memorial Institute (RPMI) 1640, modified McCoy's 5A, Ham's F10 and F12, CMRL 1066 and CMRL 1969, Fisher's medium, Glasgow Minimum Essential Medium (GMEM), Iscove's Modified Dulbecco's Medium (IMDM), Leibovitz's L-15 Medium, McCoy's 5A medium, S-MEM, NCTC-109, NCTC-135, Waymouth's MB 752/1 medium, Williams' Medium E, and the like. Cell culture media are commercially available (e.g. from GibcoBRL, Gaithersburg, Md.) and even custom-developed culture media are commercially available (see, e.g., Specialty Media, Cell and Molecular Technologies, Inc., Phillipsburg, N.J.).

The term "cytokine" refers to a protein made by cells that affects the behavior of other cells. Cytokines made by lymphocytes are often called lymphokines or interleukins (abbreviated IL). Cytokines act via specific cytokine receptors on the cells that they affect.

The term "dendritic cell" (DC) refers to any member of a diverse population of morphologically similar cell types found in lymphoid or non-lymphoid tissues. These cells are characterized by their distinctive morphology and high levels of MHC expression. DCs can be isolated from a number of tissue sources. DCs have a high capacity for sensitizing MHC-restricted T cells and are very effective at presenting antigens to T cells. The antigens may be self-antigens that are expressed during T cell development of tolerance or foreign antigens.

The term "effective amount" of a composition refers to a quantity sufficient to achieve a desired therapeutic and/or prophylactic effect, e.g., an amount which results in the prevention of, or a decrease in, the symptoms associated with a disease that is being treated. The amount administered to a subject will depend on the type and severity of the disease and on the characteristics of the individual, such as general health, age, sex, body weight, and tolerance to drugs. It will also depend on the degree, severity and type of disease. The skilled artisan will be able to determine appropriate dosages depending on these and other factors.

The term "effector cell" refers to a cell which mediates an immune response against an antigen. An example of an effector cell includes, but is not limited to, a T cell or a B cell.

The term "expansion" refers to growing cells in culture to achieve a larger homogenous population of the cells. Cells can be expanded in the presence of antigen presenting cells to produce a population of cells that is allospecific for the antigen presented by the antigen presenting cells.

The term "graft versus host disease" (GVHD) refers to a condition that occurs when T cells present in donor tissue attack the host, or recipient, of the grafted cells or tissue.

The term "HLA" is an acronym for "human leukocyte antigen" and refers to the human MHC.

The term "HLA haplotype" refers to a linked set of genes associated with one haploid genome, which determines the HLA of cells from an individual. The linked genes of the HLA are usually inherited as one haplotype from each parent. This set of genes resides on chromosome 6, and encodes cell-surface antigen-presenting proteins and many other genes.

The term "host" refers to an individual to whom transplanted cells, tissues, organs, or other biological material is transplanted. "Recipient" and "host" are used interchangeably with an equivalent meaning.

The term "immune response" refers to the concerted action of lymphocytes, antigen presenting cells, phagocytic cells, granulocytes, and soluble macromolecules produced by these cells or the liver (including antibodies, cytokines, and complement) that results in selective damage to, destruction of, or elimination from an individual's body of cells that originate from a source other than that individual's body. In cases of autoimmunity or pathological inflammation, the immune response is directed to the normal cells or tissues of the same individual rather than to nonself cells.

The term "leukocyte" refers generally to a white blood cell. Leukocytes include lymphocytes, polymorphonuclear leukocytes, and monocytes. The term "lymphocyte" refers a class of white blood cells that bear variable cell-surface receptors for antigens. The two main classes of lymphocytes are B lymphocytes (B cells) and T lymphocytes (T cells), which mediate humoral and cell-mediated immunity, respectively.

The term "preferential expansion" refers to conditions that favor the growth or proliferation of one cell type versus another in a mixed population of cells. In one embodiment, a preferential expansion of T cells refers to conditions where the number of T cells in a culture increase (on a percentage basis) to a greater extent than non-T cells in the culture. For example, a preferential expansion of T cells may be an increase in the cell number that is at least 5%, at least 10%, at least 25%, at least 50%, at least 75%, or at least 100% greater than the increase in the number of non-T cells. In one embodiment, only T cells proliferate (and non-T cells do not proliferate) in response to the culture conditions.

The term "regulatory T cell" or "Treg cell" refers to a naturally occurring subtype of T cell that can inhibit T-cell immune responses to an antigen. Treg cells represent a distinct T-cell lineage that has a key role in an individual's tolerance of self-antigens and the prevention of autoimmune disease and inappropriate immune responses. When activated, they are anergic and suppress the proliferation and cytokine production of conventional T cells. Like all T cells, Treg cells require T cell receptor activation and costimulation to become fully active.

The term "self-antigen" refers to an antigen that is expressed by a host cell or tissue.

Methods for Differentiating T Cells In Vitro

The present technology provides a method for stimulating hematopoietic stem cells or progenitor cells in culture to differentiate into T cells. Previous work in engineering the human immune system has largely relied on expansion of pre-existing mature T cells with specificity against a desired target, or introducing a specific T cell receptor into expanded mature T cells. While progenitor cells obtained from thymic tissue are capable of differentiating in culture to produce T cell receptor (TCR)-positive progeny, stem and progenitor cells obtained from other sources have not been reported to develop beyond the stage of development where TCRs rearrange and are expressed on the cell surface. Transfection of pre-rearranged TCR genes can rescue this developmental block, but the resulting T cell population is monoclonal with respect to antigen specificity. While this approach allows engineering of a T cell response against a defined target, it requires that the rearranged TCR be a pre-existing reagent that has been derived from cloned mature T cells specific for the target of interest in a patient-specific context. Thus, current approaches do not address the need to regulate the immune response in a prospective manner, and to generate a broad range of immune specificities while prohibiting the development of alloreactive clones. The value of engineering T and B cells capable of effecting normal immune responses would be profound.

The present inventors have discovered a method for the production of T lymphocytes from uncommitted hematopoietic stem or progenitor cells. This technology is distinct from the majority of immune cell cultures, which manipulate and expand mature, functional lymphocytes. The methods begin with primitive stem or progenitor cells that are cultured under conditions that promote specification of the lymphocyte lineage. These cells subsequently progress through the developmental steps that result in the selection of a repertoire of immune cells restricted to recognition of foreign antigens, and express functional receptors for recognition of a wide array of such foreign antigens. This method produces a functional immune system from a sample of the patient's own bone marrow, or from induced pluripotent stem cells derived from patient fibroblasts. In the setting of tissue transplantation, an immune system trained to recognize the graft (solid organs) or the transplant recipient (bone marrow transplants) as normal self tissue would have enormous impact on the field of transplantation. Thus, the methods provide the potential for intervention to select against immunologic specificities that may eventually lead to autoimmunity, GVHD, or graft rejection.

In one aspect, the methods for differentiating mammalian T cells in vitro include culturing precursor cells in a first culture medium for a sufficient time to produce progenitor T cells; transferring the progenitor T cells to a second culture medium, wherein the second culture medium lacks nucleotides and comprises one or more antioxidants; and culturing the progenitor T cells in the second culture medium for a sufficient time to produce differentiated T cells from the progenitor T cells. The first step is suitably carried out in an appropriate basal medium, e.g., MEM or IMDM, which can be supplemented with one or more defined cytokines as desired for optimal or appropriate cell growth. Culture conditions for individual cell types may vary, but standard tissue culture conditions form the basis of culture treatment. Typically, cells are incubated in 5% $CO_2$ incubators at 37° C. in medium. Specific chemical agents, proteins, medium components such as insulin or plasma, and certain growth or colony stimulating factors (CSFs) may be required for the maintenance of certain cell types. The second step is suitably carried out in an appropriate basal medium that lacks nucleosides and contains one or more antioxidants. In some embodiments, the second culture medium is αMEM.

The cells can be added to the first culture medium in an amount sufficient to obtain the desired expansion of the target cell or cells. Additive amounts will vary depending on the nature of the cells, the make-up of the cultured cell population and the culture conditions. The length of the culture steps can be varied to assist further in the selective proliferation of the target cell population. The final target cell enrichment may depend on when the culture is terminated. Typically, the expansion of T cells involves a culturing period of at least 3 days, but more usually, at least about 14 to about 21 days. Next the cells are transferred to a second culture medium to further promote T cell development and TCR selection. The cells are cultured for a period of at least 3 days, at least 5 days, at least 7 days, at least 10 days, at least 21 days, at least 30 days, but more usually, at least about 14 days. In some embodiments, the cells are not cultured for more than about 14 days, more than about 21 days, more than about 30 days, or more than about 45 days. Cells are cultured in standard laboratory culture plates, dishes, bottles, or other containers at an appropriate cell density. After expansion, the cells are harvested and washed with fresh culture medium before infusion to a patient.

In another aspect, the present technology provides a method of preferentially differentiating T cells over NK cells in vitro, the method comprising culturing progenitor T cells in a culture medium comprising ascorbic acid for a sufficient time to produce differentiated T cells from the progenitor T cells, while suppressing the differentiation of NK cells. In one embodiment, the medium lacks TLR ligands. The ascorbate can be any suitable form of ascorbate. In one embodiment, the ascorbate is a stabilized form of ascorbate, e.g., phosphoascorbate. The ascorbate should be added in a sufficient amount to preferentially differentiate T cells over NK cells, e.g., from about 10-1000 μg/mL, about 20-200 μg/mL, 50-200 μg/mL, 50-150 μg/mL, 75-125 μg/mL or about 100 μg/mL.

In another aspect, the present technology provides a method for differentiating NK cells in vitro comprising culturing progenitor cells in a culture medium comprising one or more TLR ligands for a sufficient time to produce differentiated NK cells from the progenitor cells, while suppressing the differentiation of T cells. One example of a suitable culture medium is MEM supplemented with one or more TLR ligands. In some embodiments, the medium lacks ascorbic acid. The term "Toll-like receptor ligand" or "TLR ligand" refers to any ligand which is capable of activating at least one of the TLRs (see e.g. Beutler, B. 2002, *Curr. Opin. Hematol.*, 9, 2-10, Schwarz et al., 2003, *Eur. J. Immunol.*, 33, 1465-1470). A TLR ligand activates at least one Toll-like receptor 1 (TLR1), TLR2, TLR3, TLR4, TLR5, TLR6, TLR7, TLR8, TLR9, TLR10, or TLR11. For example, peptidoglycan (PGN) or lipoteichoic acid (LTA) typically activates TLR2 (Aliprantis et al., *Science* (1999), 285:736-9; Underhill, et al., *Nature*, (1999), 401:811-5); double-stranded RNA, e.g. poly (I:C), typically and preferably activates TLR3 (Alexopoulou et al., *Nature* (2001), 413:732-8); lipopolysachride (LPS) typically activates TLR4 (Poltorak, et al., *Science* (1998), 282:2085-8); flagellin typically activates TLR5 (Hayashi et al. *Nature* (2001), 410:1099-103); single stranded RNA, for example bacterial RNA, and certain synthetic substances such as imidazoquinolines, typically activate TLR7 and TLR8 (Diebold S. et al. *Science* 303:1529; Heil, F H. et al. *Science* 303:1526); bacterial DNA, in particular DNA containing CpG motifs typically activates TLR9 (Schnare et al.

*Curr. Biol.* (2000), 10:1139-42; Hemmi H et al. *Nature* (2000), 408: 740-5). These cited papers are incorporated herein by reference. By referring to these incorporated papers in conjunction with general knowledge of a skilled person in the art, it is within a routine practice to test whether a molecule is a TLR ligand and whether a TLR ligand activates at least one TLR.

Sources of Starting Cell Populations

A starting cell population is selected and induced to produce the desired target cell population, i.e. T cells. In one embodiment, the starting cell population includes hematopoietic stem cells and/or progenitor cells. Hematopoietic cells are cells which are related to the production of blood cells. Exemplary hematopoietic cells include hematopoietic stem cells, primordial stem cells, early progenitor cells, CD34+ cells, early lineage cells of the mesenchymal, myeloid, lymphoid and erythroid lineages, bone marrow cells, blood cells, umbilical cord blood cells, stromal cells, and other hematopoietic precursor cells that are known to those of ordinary skill in the art. In accordance with the convention in art, the definition of hematopoietic cells excludes thymocytes. Thymocytes from the thymus are not considered "hematopoietic progenitor" cells since such cells are obtained from the thymus and are already committed.

In some embodiments, the starting cell population includes primary cells of the blood, bone marrow, body tissues or established cell lines, or cells that have been previously expanded by conventional or other means such as, for example, enriched CD34+ cells. Peripheral blood cell populations useful as the starting cell population include whole peripheral blood as well as fractions thereof such as, for example, leukophoresis cells, buffy coat cells, peripheral blood mononuclear cells (PBMNC), and low density mononuclear cells (LDMNC).

Bone marrow cells contain pluripotent stem cells which give rise to hematopoietic cells of all lineages including the lymphoid, myeloid and erythroid lineages. Stem cells have the ability to renew themselves as well as to differentiate into progenitor cells of all hematopoietic lineages. Progenitor cells retain the ability to proliferate and give rise to differentiated cells of all lineages. Differentiated cells lose the ability to proliferate and exhibit morphological characteristics specific for their lineages (such as macrophages, granulocytes, platelets, red blood cells, T cells and B cells). Bone marrow includes stem cells as well as progenitor cells of the lymphoid (T and B cells), myeloid (e.g., granulocytes, macrophages) and erythroid (red blood cells) lineages. Stem cells and progenitor cells express CD34 on their surface while differentiated cells do not. Accordingly, the detection of CD34 can be used to distinguish differentiated from undifferentiated cells.

Hematopoietic precursor cells can be derived either from the patient (autologous transplant) or from a histocompatible donor (allogeneic donor). These cells can be isolated from bone marrow, peripheral blood or from umbilical cord blood. Bone marrow typically is aspirated from the iliac crest. Bone marrow is rich in CD34+ cells; typically 1 to 2% of marrow cells are precursor cells. Peripheral blood typically contains less than 1% CD34+ cells. Umbilical cord blood is very rich in early progenitor cells and may be used as a source of cells for hematopoietic cell transplant.

The number of progenitor cells that can be harvested at one time from either source is small and, in many cases, is not sufficient for a successful transplant. Several methods have been developed to expand bone marrow cells or progenitor cells obtained from blood aphereses or from umbilical cord blood in in vitro cultures. In vitro expansion of hematopoietic stem cells requires the addition of appropriate growth factors as well as certain growth conditions provided by so called stromal cells. Stromal cells provide physical support to hematopoietic progenitor cells as well as certain growth factors required for the increase of stem cell numbers.

Separation of CD34+ cells (differentiated cells) from undifferentiated cells can be achieved by a number of different methods. The most widely used is a positive immunological selection based on binding of these cells to anti-CD34-antibodies immobilized on a solid support. Other selection methods include negative selection where all cells not expressing CD34 are isolated away from the CD34+ cells based on their expression of lineage specific cell surface antigens.

Generation of Antigen-Specific T Cells and Sources of Antigen

In one embodiment, antigen-specific T cells are activated by culturing T cells isolated as described herein above, with antigen presenting cells (APC) that have been loaded with antigen. Suitable APC are plated in culture dishes and exposed to a source of antigen as described herein, in a sufficient amount and for a sufficient period of time to allow the antigen to bind and/or be taken up by the APC. In certain aspects, antigen is exposed to the APC for a period of time between 24 hours and 4 days. In one particular embodiment, the antigen is exposed to the APC for 36, 48, or 72 hours. In a further embodiment, the antigen is exposed to the APC for 2.5, 3, 3.5, or 4 days. In certain embodiments, antigen may be exposed to the APC for periods longer than 4 days, for example 4.5, 5, 5.5, 6, 6.5, 7, 7.5, 8, 8.5, 9, 9.5, or 10 days. The amount and time necessary to achieve binding and uptake of the antigen by the APC may differ depending on the source and type of antigen and may be determined by those of ordinary skill in the art by immunoassay or binding assay. Other methods known to those of skill in the art may be used to detect the presence of antigen in the context of MHC on the APC following their exposure to antigen.

In yet an additional embodiment, PBMC (e.g., from blood, a leukapheris product, etc.) from a subject are cultured directly in the presence of antigen, as described herein, to load APC with the antigen and to activate/stimulate antigen-specific T cells present in the PBMC. In this regard, PBMC may be collected from an individual, contacted with an antigen of interest, such as a tumor antigen, or a viral lysate, etc. In this manner, the APC present in the PBMC are loaded with the antigen, which is then presented to the T cells present in the sample. In an additional embodiment, the antigen-specific T cells may be stimulated with peptide-MHC tetramers, see for example Altman, et al., *Science* 1998 Jun. 19; 280(5371): 1821.

The APC may be loaded with antigen through genetic modification. Genetic modification may comprise RNA or DNA transfection using any number of techniques known in the art, for example electroporation (using e.g., the Gene Pulser II, BioRad, Richmond, Calif.), various cationic lipids, (LIPOFECTAMINET™, Life Technologies, Carlsbad, Calif.), or other techniques such as calcium phosphate transfection as described in Current Protocols in Molecular Biology, John Wiley & Sons, New York. N.Y.

The source of antigen may be, but is not limited to, protein, including glycoprotein, peptides (including pools of overlapping peptides), superantigens (e.g., SEA, SEB, TSST-1) antibody/antigen complexes, tumor lysate, viral lysate (e.g., CMV lysate and the like), non-soluble cell debris, apoptotic bodies, necrotic cells, whole cells which are live, fixed, irradiated, heat-killed or otherwise manipulated, whole tumor cells from a tumor or a cell line that have been treated such that they are unable to continue dividing, allogeneic cells that have been treated such that they are unable to continue dividing, irradiated tumor cells, irradiated allogeneic cells, natural or synthetic complex carbohydrates, lipoproteins, lipopolysaccharides, RNA or a translation product of said RNA, and DNA or a polypeptide encoded by said DNA.

The antigen may comprise viral antigens such as CMV pp 65, HIV pg120, and the like. In certain embodiments, antigen may comprise defined tumor antigens such as the melanoma antigen Melan-A (also referred to as melanoma antigen recognized by T cells or MART-1), melanoma antigen-encoding genes 1, 2, and 3 (MAGE-1, -2, -3), melanoma GP100, carcinoembryonic antigen (CEA), the breast cancer angtigen, Her-2/Neu, serum prostate specific antigen (PSA), Wilm's Tumor (WT-1), PR1, PR3 (antigens implicated in the graft-versus-leukemia (GVL) effect in chronic myeloid leukemia), mucin antigens, MUC-1, -2, -3, -4, B cell lymphoma idiotypes, and the like. The skilled artisan would appreciate that any tumor antigen would be useful in the context of the present invention.

Pharmaceutical Compositions

In another aspect, the present technology provides a pharmaceutical composition comprising a T cell or NK cell population in a formulation which is suitable for administration to a patient in need thereof. In some embodiments, the T cells are specific for an antigen associated with an autoimmune or inflammatory disease. In some embodiments, the T cells are useful for promoting transplant tolerance. The methods of generating antigen-specific T cells described herein are useful for generating the T cell population for use in the composition according to this embodiment.

The pharmaceutical composition comprising T cells is administered to a subject in need thereof in a manner appropriate to the disease to be treated and/or prevented. The quantity and frequency of administration will be determined by such factors as the condition of the patient and the type and/or severity of the patient's disease. Appropriate dosages may also be determined by clinical trials. An effective amount of the composition can be determined by a physician with consideration of individual differences in age, weight, disease severity, condition of the patient, route of administration and any other factors relevant to treatment of the patient. In general, a pharmaceutical composition comprising T cells may be administered at a dosage of about $10^5$ to $10^8$ cells/kg body weight, suitably $10^5$ to $10^6$ cells/kg body weight, including all integer values within these ranges. The compositions may also be administered multiple times at these dosages. The optimal dosage and treatment regime for a particular patient can readily be determined by one skilled in the art of medicine by monitoring the patient for signs of disease and adjusting the treatment accordingly. The cells can be administered by using infusion techniques that are commonly used in immunotherapy, and may be administered to a patient subcutaneously, intradermally, intramuscularly, or by intravenous injection.

These methods described herein are by no means all-inclusive, and further methods to suit the specific application will be apparent to the ordinary skilled artisan. Moreover, the effective amount of the compositions can be further approximated through analogy to cells and compositions known to exert the desired effect.

EXAMPLES

The present methods, thus generally described, will be understood more readily by reference to the following examples, which are provided by way of illustration and are not intended to be limiting of the present methods.

Example 1

Promoting T Cell Development from Mouse Bone Marrow Stem and Progenitor Cells Through the TCR Selection Stage in Culture In this Example, several important variables that are important to the successful development of T lymphocytes from bone marrow-derived cells were identified. Our results indicate that the basal culture conditions optimal for bone marrow progenitor cells differ from those optimal for thymocytes, and we have identified several components of basal culture medium that regulate the process of TCR selection. Our experiments defining optimal culture conditions tell us that in order to promote T cell development from bone marrow-derived progenitor cells, a two-stage culture system is required. In the first stage, bone marrow cells are expanded under the influence of lymphoid-specifying cytokines (IL-7 and Flt3 ligand) and notch signaling delivered by OP9-DL1 cells. The expansion of the resulting pro-T cells is robust, reaching a total expansion of $10^5$-fold or more (FIG. 1).

All cultures were initiated by seeding $2 \times 10^3$ FACS-sorted bone marrow progenitor cells, selected based on the surface phenotype c-kit+Sca-1+Thy-1.1-neg lineage-neg, onto a feeder layer of OP9-DL1 stromal cells. All cultures contained 1 ng/ml IL-7 and 5 ng/ml Flt3L and otherwise identical additives (10% fetal calf serum, stabilized alanyl-glutamine, antibiotics, 2-ME, supplemental amino acids, and supplemental vitamins).

Figure 2:
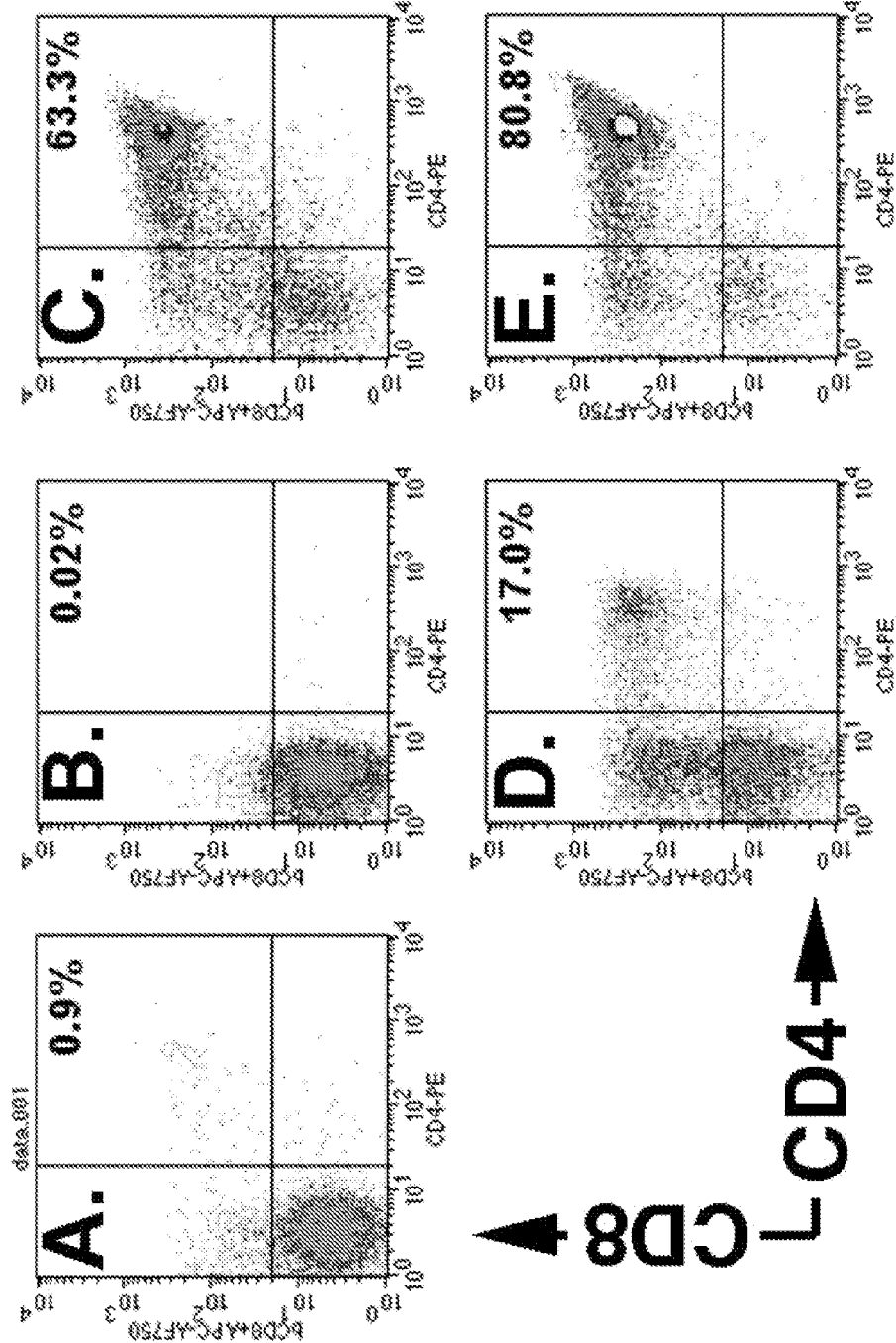
FIG. 2 shows the effect of basal medium and switch cultures on pro-T cell expansion and selection by TCR signaling in vitro. All cultures were initiated with $2 \times 10^3$ cells from one bone marrow progenitor pool. Differentiation of T cells was tracked based on expression of CD4 and CD8.

Maintenance of cultures at this stage of development can be achieved for about 30 days, but T cell development will proceed inefficiently unless the cultures are switched into conditions that are conducive to T lineage differentiation. Operationally, this switch was achieved changing the basal culture medium from minimal essential medium (MEM) to the alpha modification of MEM (αMEM). Initiation of bone marrow cultures in αMEM fails to promote efficient expansion of progenitor cells, but progenitor cells expanded in MEM under the influence of IL-7, Flt3L, and notch signaling are poised to progress through TCR selection once shifted into αMEM. (FIG. 2). The switch culture conditions enhanced the yield of CD4/CD8 double positive (DP) cells by about 10-fold. Cell numbers were determined by hemocytometer counting at each passage. Cultures were passaged every 3-4 days, and appropriate dilutions were made to maintain a cell density of less than $5 \times 10^5$ cells/ml. The cell counts were corrected by a factor corresponding to the product of these dilutions. The percentage of CD4+CD8+ DP cells was determined by FACS analysis. The total yield of cells that passed TCR selection, based on the DP phenotype, is indicated in Table 1.

TABLE 1

| Culture Medium | Day 14 | | | Day 24 | | |
|---|---|---|---|---|---|---|
| | Cell Number | Percent DP | Number DP | Cell Number | Percent DP | Number DP |
| IMDM | $3.0 \times 10^6$ | 0.9 | $2.7 \times 10^4$ | $4.4 \times 10^7$ | 28.5 | $1.3 \times 10^7$ |
| MEM | $2.5 \times 10^6$ | 0.02 | $5.0 \times 10^2$ | $3.6 \times 10^7$ | 16.2 | $5.8 \times 10^6$ |
| αMEM | $5.0 \times 10^5$ | 63.3 | $3.2 \times 10^5$ | $5.1 \times 10^6$ | 54.3 | $2.8 \times 10^6$ |
| MEM to αMEM | ND | | | $3.2 \times 10^7$ | 80.8 | $2.6 \times 10^7$ |

Figure 3:
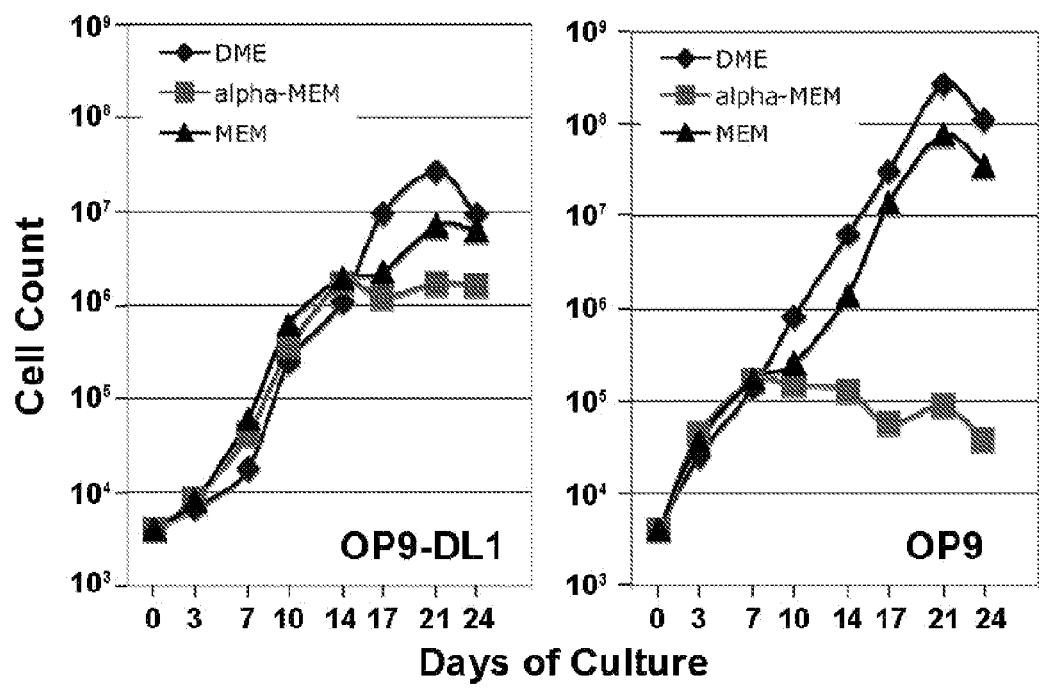
FIG. 3 shows a comparison of cellular expansion in T cell conditions (left panel) or B cell conditions (right panel) in different basal media. Cultures maintained in αMEM fail to maintain proliferation in B cell conditions (right panel) but promote selection by TCR signaling in T cell conditions (as shown in FIG. 2) and allow continued expansion of T cells (left panel).

To address the mechanism behind the ability of switch cultures to promote efficient TCR selection and subsequent T cell maturation, we evaluated the formulations of MEM and αMEM. These basal media differ in a large number of components, with αMEM including additional amino acids, nucleosides, anti-oxidants, and vitamins. We have systematically evaluated many of the components that distinguish these two basal media and other culture medium formulations (IMDM, RPMI-1640, and DME) and have established the anti-oxidant components as a major factor in regulating the ability of the switch cultures to promote T cell maturation. We hypothesize that the sensitivity of bone marrow stem cells to oxidative stress is managed in part by the hypoxic nature of the bone marrow environment, and that in fact anti-oxidants inhibit the differentiation of bone marrow derived cells in culture. As evidence supporting this hypothesis, we have observed that B cell expansion and differentiation is markedly suppressed in cultures established in αMEM versus other basal media (FIG. 3). Several other components in αMEM also influence efficient T cell maturation, including nucleosides and ammonium ions derived from decomposition of glutamine, but these are mainly negative influences on proliferation and differentiation as shown in FIG. 1. The presence of nucleosides in the culture medium inhibits the activity of ribonucleotide reductase and limits the availability of nucleoside precursors intracellularly. It is well known that developing T lymphocytes are very sensitive to inhibition of proliferation and undergo apoptosis in the presence of exogenous nucleosides. We hypothesize that the switch cultures facilitate TCR selection by suppressing the robust proliferation of the pro-T cells in the cultures. This cell-cycle arrest is necessary for the initiation of DNA rearrangement in order to generate rearranged TCRβ protein for subsequent β selection. However, initiation of OP9-DL1 cultures containing bone marrow-derived progenitor cells in αMEM prevents robust expansion of pro-lymphocytes and in many cases blocks progression to the DP stage. Fetal liver and thymic cells are not as sensitive to this block in proliferative expansion, which explains why the OP9-DL1 culture models works best with these two starting populations.

Figure 4:
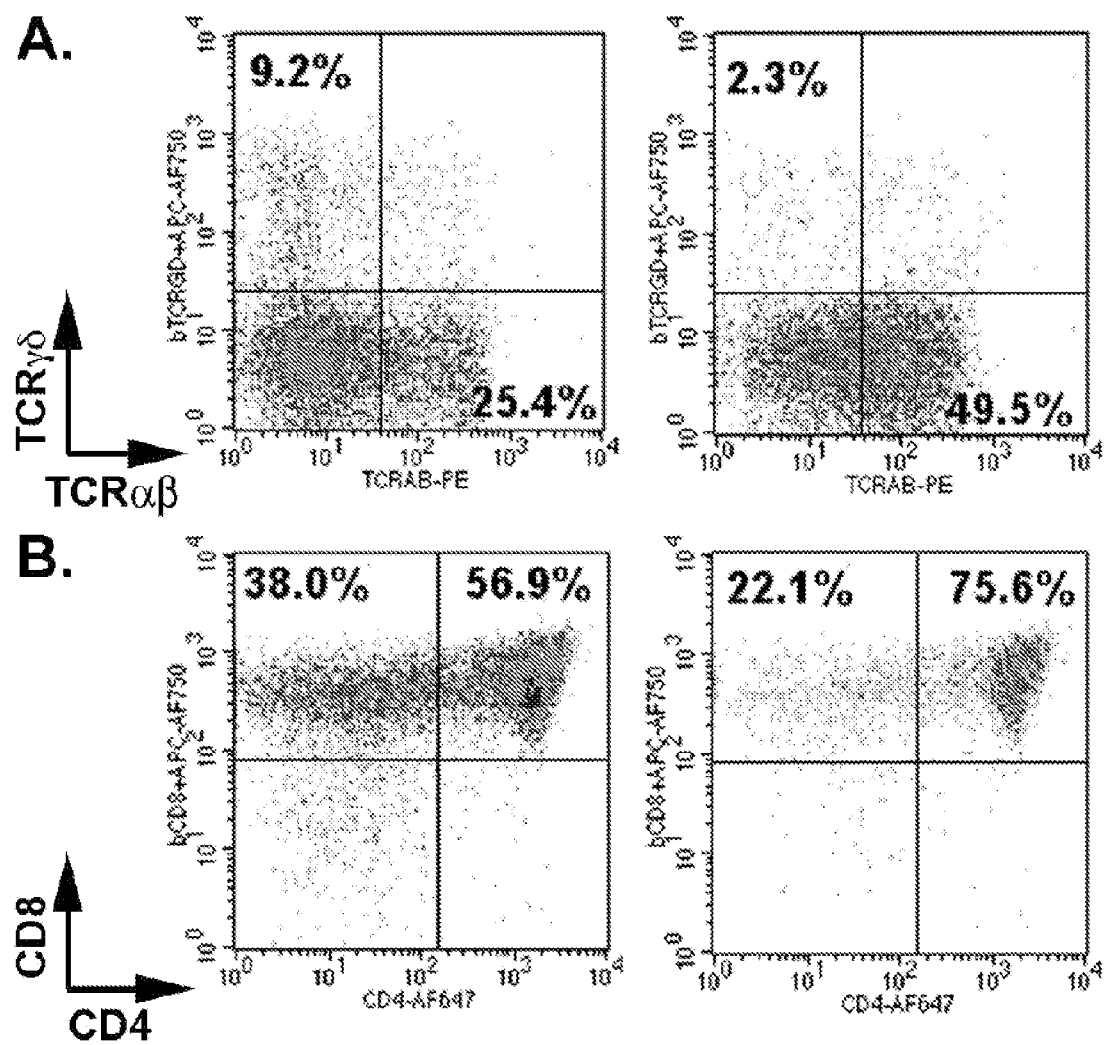
FIG. 4 shows analysis of selection by TCR signaling in OP9-DL1 cultures.

To confirm our interpretation that switch cultures promote the process of TCR selection, we evaluated expression of the two forms of TCR (TCRαβ and TCRγδ) on T cells obtained after culture of bone marrow progenitors with OP9-DL1 stromal cells. As shown in FIG. 4A, cultures initiated in IMDM for 14 days and then switched to αMEM showed a marked increase in TCRαβ+ cells with a concomitant decrease in TCRγδ+ cells when analyzed two weeks after the switch, in comparison to cultures maintained in IMDM. Analysis of TCRαβ expression with respect to CD4 and CD8 expression (FIG. 4B) shows that 75.6% of the TCRαβ cells in the culture express both CD4 and CD8, consistent with successful TCRαβ selection. FIG. 4B also shows that many of the CD8+ CD4− cells in the culture lack TCRαβ. This suggests that these CD8+CD4− cells represent either an intermediate stage that occurs prior to TCR selection (immature CD8 single positive cells) or are CD8+ DC. We have data supporting the latter conclusion, based on analysis of CD11c expression (data not shown). It is therefore possible that endogenous DC derived from the bone marrow progenitor population may participate in the process of immune education in these cultures.

Example 2

Opposing Effects of Toll-Like Receptor Ligands and Ascorbic Acid on T and NK Cell Development from Lymphoid Progenitor Cells The OP9-DL1 stromal line is an important tool in the in vitro culture lymphocytes. Lymphocyte progenitors (KLS, Thy1.1-) harvested from adult murine bone marrow and seeded on this stromal line can be followed through stages of maturation by immunophenotyping. We observed that addition of stem cell factor (SCF), contaminated with lipopolysaccharide (LPS) through its production in E. coli, was particularly effective at promoting NK cell development in the OP9-DL1 culture system. Toll-like receptors, an important component of anti-microbial defense by the innate immune response, recognize LPS and other microbial products. Toll-like receptor ligands (TLR-L) have been shown to enhance NK cell proliferation, however an effect on NK cell differentiation from progenitor cells has not been established. A separate set of experiments led us to hypothesize that ascorbic acid (vitamin C) promotes T cell differentiation.

We therefore designed experiments to evaluate the differential effects of TLR-L and ascorbic acid on NK and T cell development from lymphoid progenitors co-cultured with OP9-DL1 stromal cells. Lymphocyte progenitor cells (KLS, Thy1.1-) were sorted from adult mouse bone marrow and 1000-2000 progenitor cells were seeded per well in a 24 well plate coated with OP9-DL1 stroma. Cultures were supplemented with IL-7 (5 ng/ml), Flt3 ligand (5 ng/ml), and SCF (100 ng/ml) plus one of 5 different TLR-L (TLR1/2, TLR3, TLR4, TLR5, and a crude LPS preparation that likely contains a number of TLR-L), with or without addition of a stabilized form of ascorbic acid, phosphoascorbate at a final concentration of 250 μg/ml. Cells were passaged, counted and re-seeded with fresh media and supplements twice a week over a 30-day period. Immunophenotype and viability were evaluated by flow cytometry. Markers for T cell development included CD44, CD25, CD3, CD4, CD8, T cell receptor 13 chain and T cell receptor γδ chains. NK cells were evaluated for the presence of NKp46, NK1.1, and DX5.

Figure 5:
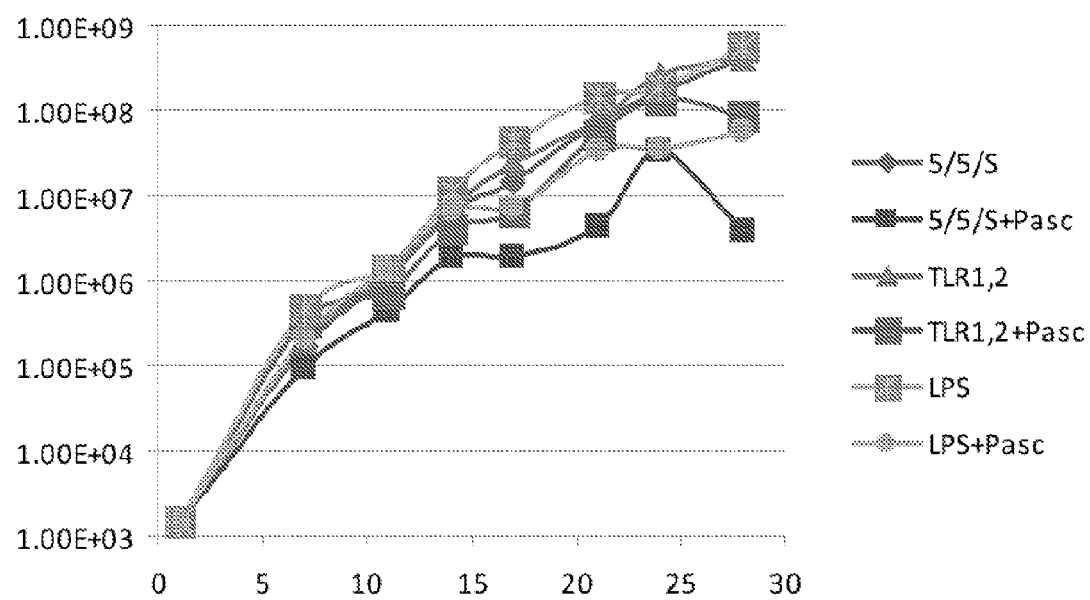
FIG. 5 is a growth curve showing 28 day culture expansion under various culture conditions.
Figure 6:
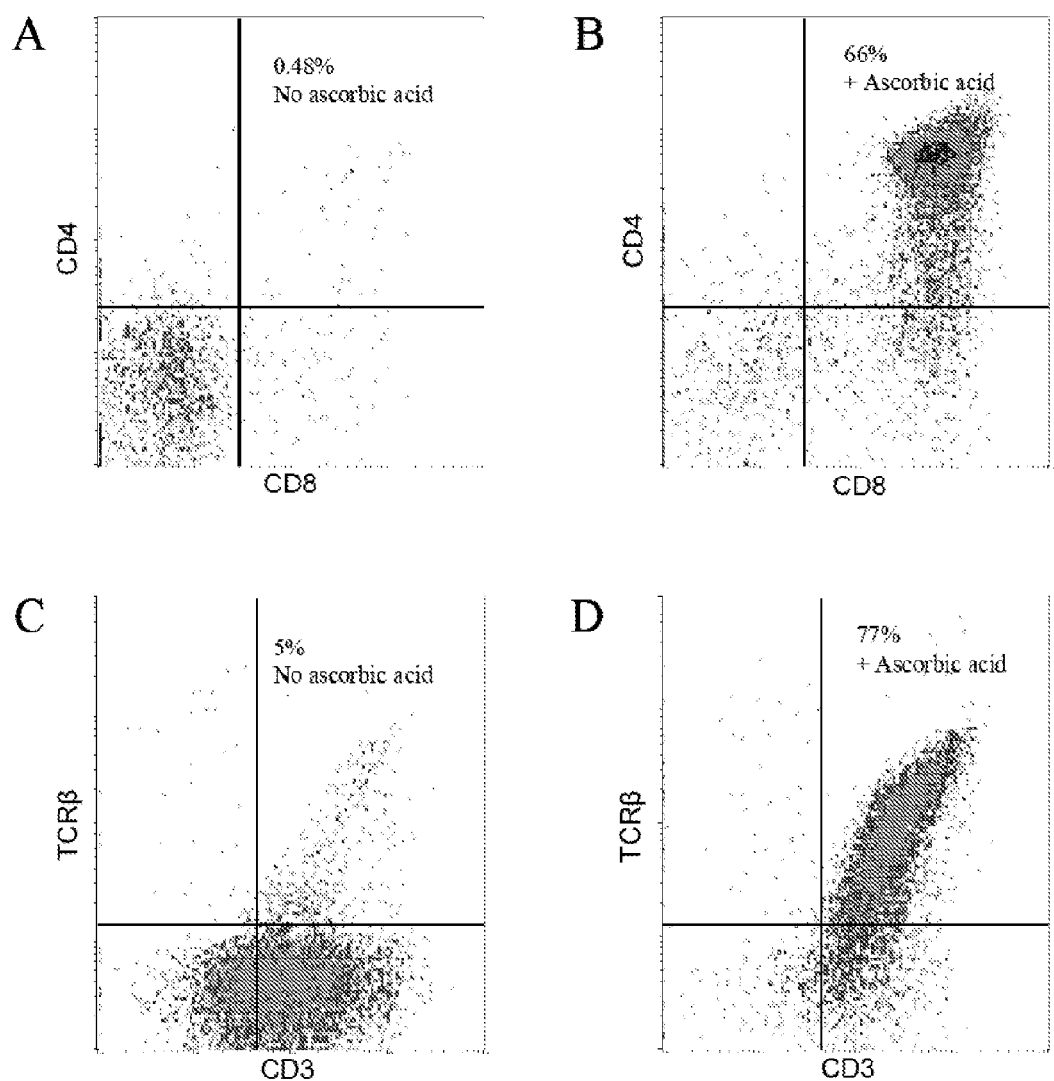
FIG. 6 shows T cell development, with 2 left panels representing 28 day old cultures without ascorbic acid and the right panels representing addition of ascorbic acid. Upper panels (FIG. 6A and FIG. 6B) show CD4/CD8 co-expression, lower panels (FIG. 6C and FIG. 6D) show TCRβ/CD3 co-expression.
Figure 7:
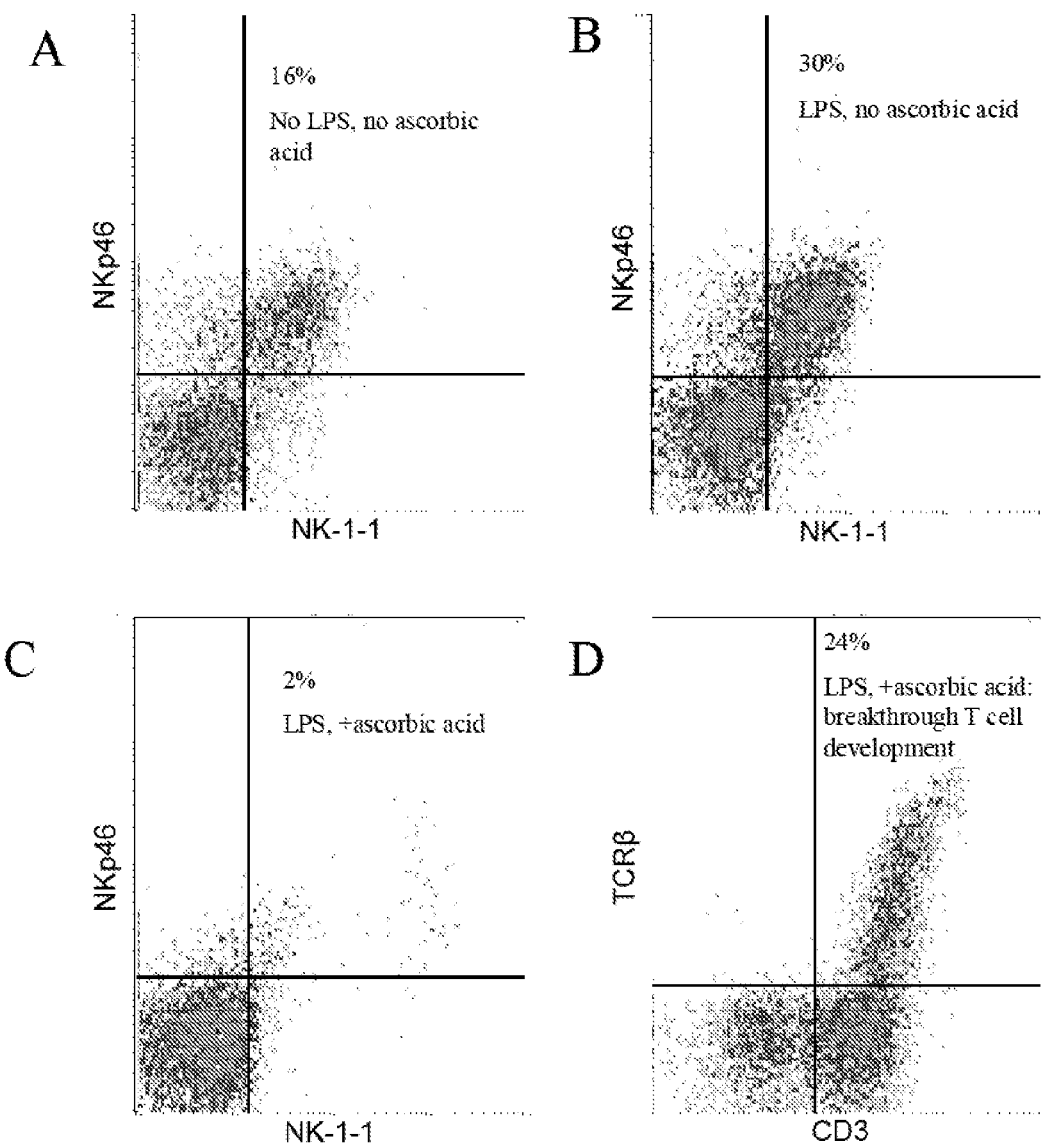
FIG. 7A shows NK cell development represented by NK1.1 and NKp46 co-expression.
FIG. 7B shows increased NK cells with addition of LPS.
FIG. 7C shows detrimental effect of ascorbic acid on NK cell development.
FIG. 7D shows preferential T cell development with the addition of ascorbic acid based on TCRβ and CD3 co-expression.

We observed robust cell expansion, inhibited somewhat by addition of ascorbic acid. (FIG. 5). The inhibitory effect of ascorbate on expansion was most pronounced in the culture condition lacking TLR-L. T cell differentiation was markedly advanced by the addition of ascorbic acid in the absence of TLR-L, with the majority of cells co-expressing CD4/CD8 and TCR13/CD3. (FIG. 6). The addition of different TLR-Ls inhibited T cell differentiation, and this inhibition was partially rescued by addition of ascorbic acid. NK cell differentiation, defined as co-expression of NKp46 and NK1.1, was two to three-fold greater with the addition of TLR1/2, TLR4, TLR5, and crude LPS compared to cultures lacking TLR-L addition. (FIG. 7). In each of these conditions, NK cell differentiation was markedly inhibited by addition of ascorbic acid.

Our data supports the hypothesis that both T and NK cell progenitors require Notch signaling for differentiation. In our in vitro model, differentiation of one lineage at the expense of the other can be manipulated with addition of TLR-L or ascorbic acid. Addition of bacterial TLR-L promotes NK cell differentiation at the expense of T cell differentiation; an effect that is partially overcome with the addition of ascorbic acid. The addition of ascorbic acid promotes robust T cell differentiation, and inhibits significant NK cell differentiation in all conditions. The ability of ascorbic acid to promote T cell differentiation appears to dominate over TLR-L promotion of NK lineage differentiation. These findings demonstrate a method for ex vivo expansion of immune cells for therapeutic use.

Example 3

Figure 8:
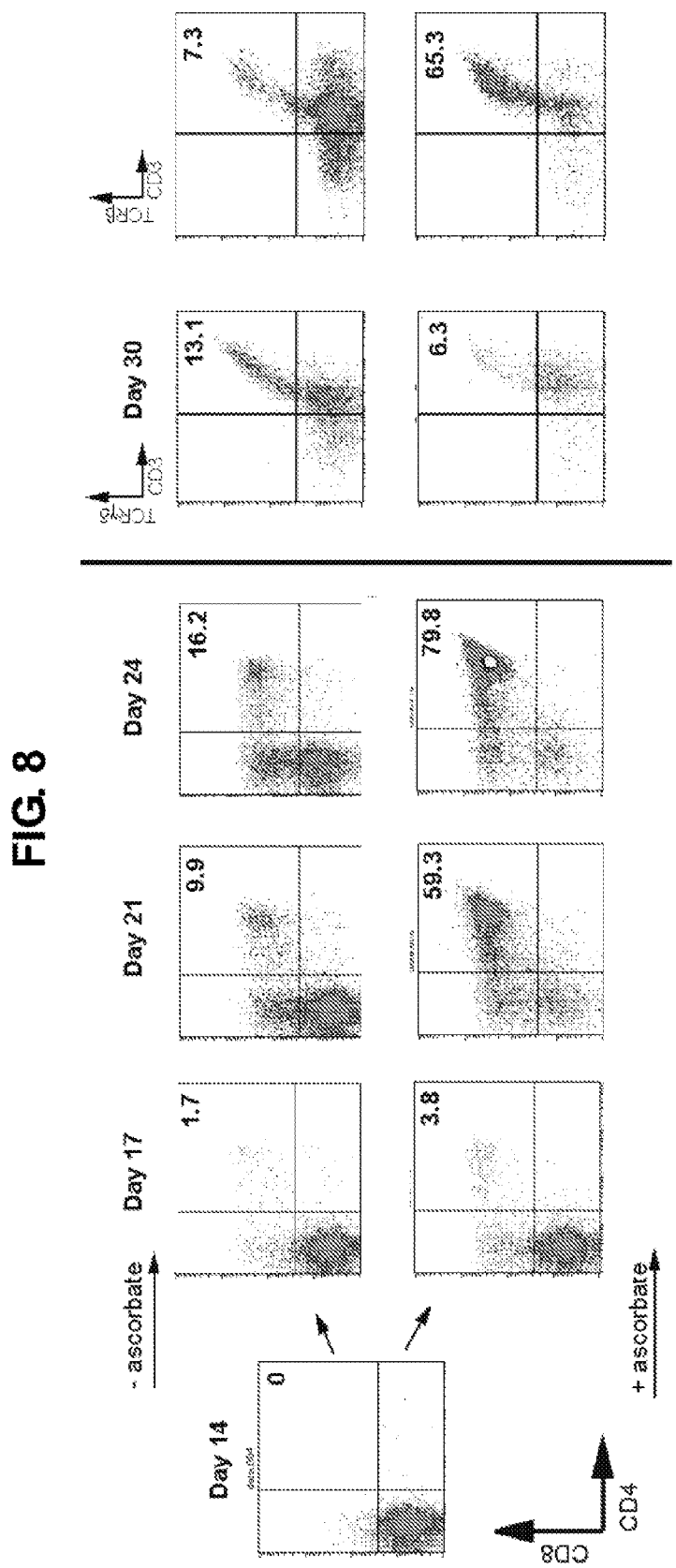
FIG. 8 shows modulation of T cell development by ascorbic acid.

Determination of Mechanism of Action of Ascorbate in Promoting T Cell Differentiation To establish the mechanism by which ascorbic acid promotes T cell development, we initially tested whether the anti-oxidant activity of ascorbic acid plays a key role. To test this, mouse lymphoid progenitor cells were isolated from adult bone marrow tissue by flow sorting, based on the phenotype c-kit+Sca-1+ lineage-neg CD90.1-neg, and 1000-2000 cells were plated per ml in the presence of the cytokines IL7 and Flt3L and the stromal cell line OP9-DL1. Cultures were harvested by forceful pipetting every 3-4 days and reseeded on a fresh monolayer of OP9-DL1 cells. After 14 days in culture, the cell number had expanded approximately 1000-fold (data not shown). At this point, the culture was split into two conditions, with one set of cultures supplemented with 1-ascorbic acid-2-phosphate (250 μg/ml), and the passages were continued through 30 days. As shown in FIG. 8, a sample of the each culture was evaluated at 3 to 4 day intervals for expression of CD4 and CD8 (left panels) or T cell receptor δβ or β chains complexed with CD3 (right panels). Numbers indicate the percentage of cells with co-expression of CD4 and CD8 or CD3 and TCR. By day 30, cultures lacking ascorbate had expanded almost one million-fold, while ascorbate had induced differentiation that was accompanied by a proliferative arrest, leading to an overall expansion of 5000-fold. The differentiating effect of ascorbate was not reproduced by other anti-oxidants (N-acetyl-cysteine, 1-cysteine, or alpha-lipoic acid; data not shown), suggesting that an activity of ascorbate apart from or in addition to redox regulation is responsible.

Example 4

Ascorbate Promotes Increased mRNA Expression of Rearranged TCRα and TCRβ Genes During In Vitro T Cell Development To further address the mechanism of how addition of a stabilized form of vitamin C, phospho-ascobate (pAsc), to culture media promotes T lineage differentiation, we employed quantitative RT-PCR and spectratyping analysis to examine mRNA expression of rearranged complementarity-determining region 3 (CDR3) polymorphisms in T cell receptor β (TCRβ) variable (BV) and TCRα variable (AV) genes in the presence or absence of pASC. Lymphocyte progenitor cells (KLS, Thy1.1-) were sorted from adult mouse bone marrow and 1000-2000 progenitors were seeded per well in a 24 well plate coated with OP9-DL1 stromal cells. Cultures were supplemented with IL-7 (5 ng/ml) and Flt3 ligand (5 ng/mL) plus or minus pAsc (100 μg/mL). Cells were passaged, counted and reseeded with fresh media and supplements twice a week over a 21 day period. Immunophenotype and viability were evaluated by flow cytometry. Markers for T cell development included CD44, CD25, CD3, CD4, CD8, TCRβ chain and TCRγδ chains. Total RNA from cultured cells was isolated at day 21, reverse transcribed to cDNA, and analyzed by RT-PCR for differential expression of BV and AV genes using gene-specific primers for BV1, BV4, BV8.2, BV13, AV2, and AV8 with corresponding beta constant (BC) and alpha constant (AC) primers. For spectratyping, RT-PCR amplicons were generated using BV or AV gene-specific primers for BV1, BV4, BV8.2, BV13, AV1, AV2, AVS, AV8, AV10, AV13, AV16, AV18, and AV19 with corresponding BC and AC primers. These products were then re-amplified with the same gene-specific primers but with fluorochrome-labeled nested BC or AC primers. Spectratype analysis was performed on labeled amplicons by capillary electrophoresis.

Figure 9:
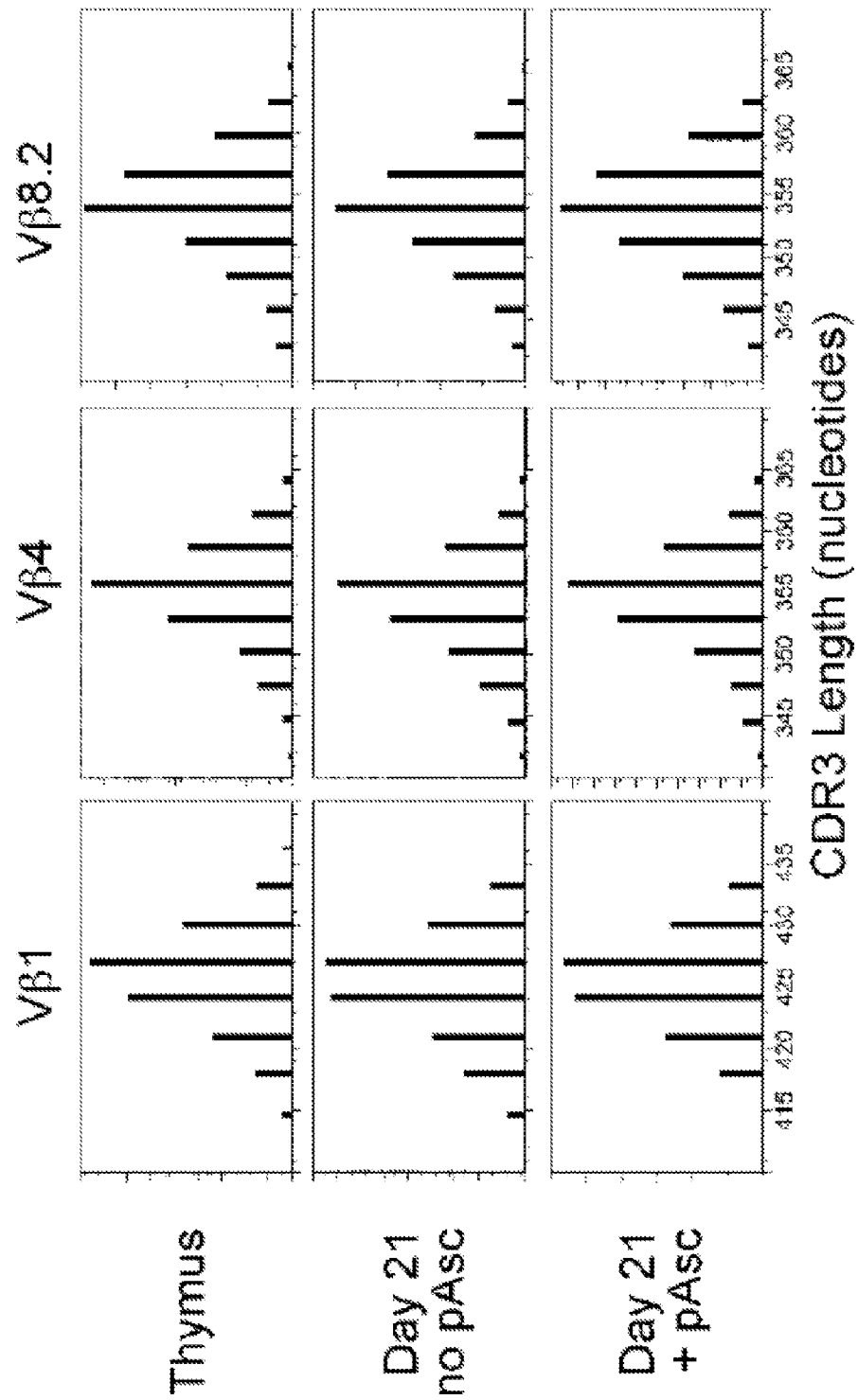
FIG. 9 shows spectrotype analysis of TCRβ gene rearrangements following capillary electrophoresis of PCR amplicons generated from nested constant region primers and Vβ specific primers. The X-axis shows the base pair length of complementarity-determining region 3 (CDR3) while the Y-axis shows relative signal strength. The distribution of CDR3 lengths is spaced in 3 nucleotide intervals, consistent with selection for gene rearrangements that preserve the translational reading frame through the rearranged region of the TCR. This result is seen regardless of whether phosphoascorbate (pAsc) was included in the cultures at 250 μg/ml. This data shows that the first checkpoint of T cell development, 13 selection, does not require ascorbate.
Figure 10:
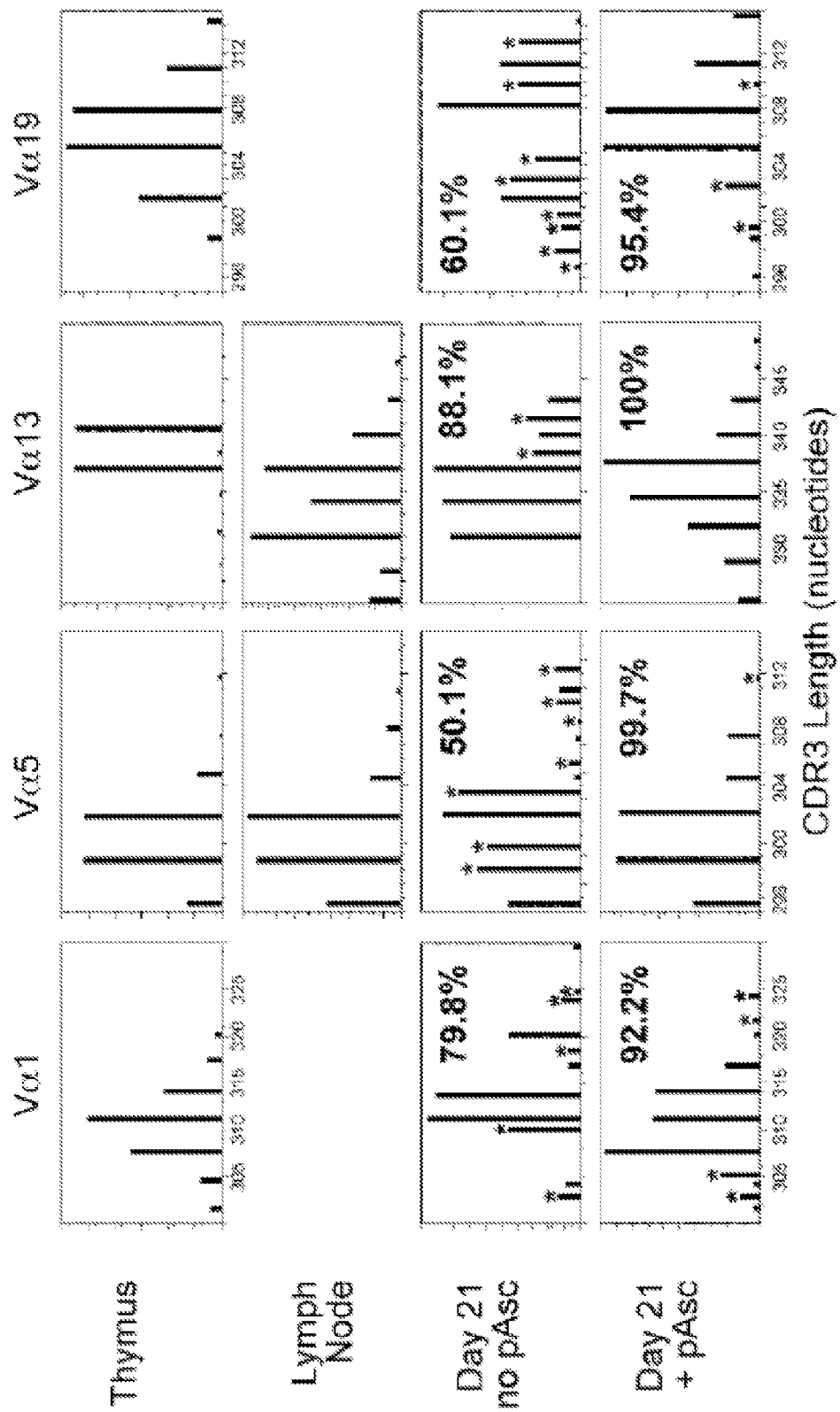
FIG. 10 shows spectrotype analysis of TCR α gene rearrangements following capillary electrophoresis of PCR amplicons generated from nested constant region primers and Vα specific primers. The X-axis shows the base pair length of complementarity-determining region 3 (CDR3) while the Y-axis shows relative signal strength. Asterisked bars represent likely non-functional, out of frame transcripts based on nucleotide length comparison to thymic or lymph node positive control. Percentages are amount of in frame signal within each distribution. Taken together with FIG. 9, these data suggest that phosphoascorbate (pAsc) exerts its effect temporally after β selection by enhancing signal transduction through the mature TCR.

The results of this analysis showed that T cell differentiation was markedly advanced by the addition of pAsc, with the majority of cells co-expressing CD4/CD8 and TCR beta/CD3. Transfection of a functionally rearranged TCR beta gene failed to rescue cells cultured without pAsc to the double positive stage; similar results were obtained with bone marrow cells derived from TCR alpha-beta transgenic donor mice. Cells cultured with pAsc demonstrated an average 5 fold increase (5.08±0.40) in expression of BV genes and an average 13 fold increase (13.46±2.18) of AV genes. As shown in FIG. 9, pAsc did not induce alterations in the spectratype distributions of BV amplicons compared those generated under non-pAsc conditions or to distributions derived from thymic cDNA. This data indicates that the first checkpoint in T cell development, termed "β-selection", is not influenced by pAsc. However, as shown in FIG. 10, spectratype distributions of AV amplicons generated under pAsc conditions more closely resembled those derived from thymic and lymph node cDNA than distributions generated from non-pAsc conditions. Cultures maintained in the absence of pAsc resulted in many complementarity-determining region-3 (CDR3) length polymorphisms that were not spaced by three nucleotides (indicated by the asterisks in FIG. 10) and thus would not be properly translated to a functional TCRα polypeptide. The numbers in each panel of FIG. 10 indicate the percentage of amplicons that maintain the spacing of three nucleotides that is necessary for proper translation of functional TCRα polypeptides from the mRNA. Cultures maintained in the absence of pAsc ranged from 50 to 88% in-frame rearrangements. In contrast, cultures that included pAsc showed a higher frequency of proper rearrangements based on the CDR3 length polymorphism analysis (92 to 100% in-frame rearrangements). Coupled with the quantitative analysis of gene expression showing a 13-fold increase in expression of AV genes, this result shows that developing T cells with a properly rearranged TCRα gene are selected for growth in the presence, but not the absence, of pAsc.

Example 5

Ascorbate Promotes Increased DNA-binding activity of AP-1, NF-1, and C/EBP in Developing T Lymphocytes Previous studies of the action of ascorbate have focused on scurvy, and the requirement for the reducing activity of ascorbate to function as a co-factor for prolyl hydroxylase during the assembly of collagen. Recent publications have shown that prolyl hydroxylases also regulate several redox-sensitive transcription factors, including the hypoxia-inducible factors (HIF family) activating protein-1 (AP-1), NFκB, and CREB family members (8). Ascorbate has been shown to promote transcription of AP-1 subunits, and to modulate binding of AP-1 to DNA in a post-translational manner (9). In addition, enzymes containing iron-sulphur clusters catalyze nucleoside metabolism, chromatin modifications, and DNA repair, and these enzymes may require ascorbate as a co-factor in a manner analogous to prolyl hydroxylases (10). We have performed a microarray analysis of developing lymphocytes 24, 72, and 96 hours after addition of ascorbate, and our results showed that AP-1 and other transcription factors implicated in thymocyte development are expressed in our cultured cells but that expression is not markedly upregulated by ascorbate. However, our microarray analysis clearly showed upregulation of previously defined AP-1 target genes. Therefore, we hypothesize that ascorbate functions at a post-transcriptional level by modulating the activity of AP-1 or other transcription factors. Previous studies have established that a spectrum of transcription factors, including AP-1, regulate T cell development at various stages including TCR signaling (11).

Figure 11:
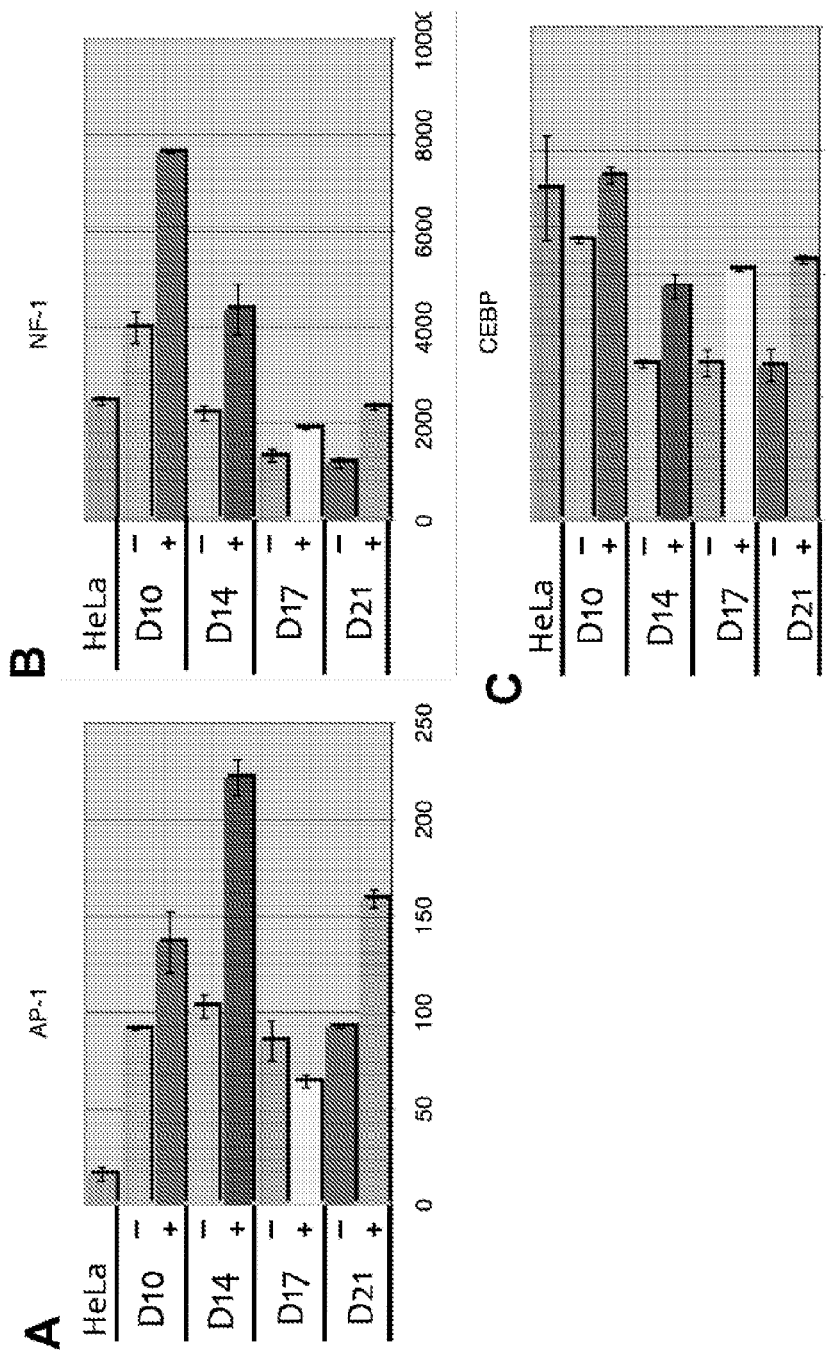
FIGS. 11A-11C shows the identity of three transcriptional regulators (AP-1, NF-1, and C/EBP, respectively) that are upregulated in lymphocytes developing in the presence of 250 μg/mL ascorbate versus in the absence of ascorbate (indicated at individual days of culture by the + and − signs, respectively). Of these, AP-1 is a well-established component of the TCR signal transduction pathway that is known to be stimulated by ascorbic acid.

There are several approaches to establish which of these changes in gene expression are responsive to ascorbate. As an example, a screen is performed using protein analysis kits, such as those available from Panomics. The Procarta TF plex kit or a similar product is used to provide quantitative analysis of panels of 40 or more transcription factors based on their binding to target nucleotide sequences. These experiments involve isolation and culture of bone marrow progenitor cells as shown in FIG. 8. Ascorbate is added to cultures to promote lymphocyte differentiation after approximately 14 days, and cell lysates prepared from lymphocyte differentiation cultures 1 to 3 days after ascorbate addition. Control cultures are carried in parallel but without ascorbate addition. Lysates are screened using the Procarta TF plex kit, in which the presence of functional transcription factors is detected after capture of the transcription factors—specific probes on Luminex fluorescent beads. The beads are intrinsically fluorescent in two colors, allowing for the identification of specific transcription factors, while quantification of transcription factor binding is evaluated in a third color channel. Analysis is performed on a Luminex instrument, or by flow cytometry. This type of experiment reveals transcription factors that are regulated in developing lymphocytes by ascorbate, either at the transcriptional level or post-transcriptionally. Transcription factors detected in the preceding screen could be further validated using gel shift assays, available in kit form from Panomics. The results of such a screen identified several transcription factors, including AP-1, NF-1, and C/EBP to be upregulated in developing lymphocytes by ascorbate (FIG. 11). Since AP-1 is known to be critical in transduction of signals generated by TCR, this result is consistent with the hypothesis that ascorbate promotes T cell development by enhancing the growth of pre-T cells that have successfully rearranged and expressed a functional TCRα polypeptide in association with a functional TCRβ polypeptide and the CD3 complex. The growth enhancement may be due to an increase in the activity of AP-1, which is necessary for efficient transduction of growth-promoting signals through the TCR-CD3 complex.

Summary.

In our in vitro model, the addition of pAsc promotes robust differentiation of adult mouse bone marrow progenitors to T cells co-expressing CD4/CD8 and a functional TCRαβ. However, the mechanism by which pAsc exerts its effect remains elusive. We suspect that pAsc enhances an already pre-programmed process. The fact that transfection of a functional TCR beta gene fails to rescue differentiation, coupled with our observation that pAsc has no effect on BV spectratypes suggests that enhancement of β-selection is not involved. Rather, the AV spectratyping data suggest that pAsc exerts its effect temporally near TCRα gene rearrangement, possibly via enhancement of the TCR signal transduction cascade by enhancement of AP-1 activity.

REFERENCES

1. Paulos C M, Suhoski M M, Plesa G, Jiang T, Basu S, Golovina T N, Jiang S, Aqui N A, Powell D J, Jr., Levine B L, Carroll R G, Riley J L, June C H. Adoptive immunotherapy: good habits instilled at youth have long-term benefits. *Immunol Res.* 2008; 42:182-196.)
2 and 3. Schmitt T M, Zuniga-Pflucker J C. Induction of T cell development from hematopoietic progenitor cells by delta-like-1 in vitro. *Immunity.* 2002; 17:749-756.
4. Zakrzewski J L, Kochman A A, Lu S X, et al. Adoptive transfer of T-cell precursors enhances T-cell reconstitution after allogeneic hematopoietic stem cell transplantation. *Nat. Med.* 2006; 12:1039-1047
5. Schmitt T M, Ciofani M, Petrie H T, Zuniga-Pflucker J C. Maintenance of T cell specification and differentiation requires recurrent notch receptor-ligand interactions. *J Exp Med.* 2004; 200:469-479.
6. Huang J, Garrett K P, Pelayo R, Zuniga-Pflucker J C, Petrie H T, Kincade P W. Propensity of adult lymphoid progenitors to progress to DN2/3 stage thymocytes with Notch receptor ligation. *J. Immunol.* 2005; 175:4858-4865.
7. Dai B, Wang P. In vitro differentiation of adult bone marrow progenitors into antigen-specific CD4 helper T cells using engineered stromal cells expressing a notch ligand and a major histocompatibility complex class II protein. *Stem Cells Dev.* 2009; 18:235-245.
8. Siddiq A, Aminova L R, Ratan R R. Prolyl 4-hydroxylase activity-responsive transcription factors: from hydroxylation to gene expression and neuroprotection. *Front Biosci.* 2008; 13:2875-2887.
9. Lopez-Lluch G, Blazquez M V, Perez-Vicente R, et al. Cellular redox state and activating protein-1 are involved in ascorbate effect on calcitriol-induced differentiation. *Protoplasma.* 2001; 217:129-136.
10. Simmons J M, Muller T A, Hausinger R P. Fe(II)/alpha-ketoglutarate hydroxylases involved in nucleobase, nucleoside, nucleotide, and chromatin metabolism. *Dalton Trans.* 2008:5132-5142.
11. Georgescu C, Longabaugh W J, Scripture-Adams D D, et al. A gene regulatory network armature for T lymphocyte specification. *Proc Natl Acad Sci USA.* 2008; 105:20100-20105.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for differentiating mammalian T cells in vitro, the method comprising:
    culturing hematopoietic stem cells, hematopoietic progenitor cells, or both hematopoietic stem cells and hematopoietic progenitor cells in a first culture medium for a sufficient time to produce progenitor T cells, wherein the first culture medium lacks ascorbate and comprises cells modified to express a notch ligand configured to direct differentiation of T cells;
    transferring the progenitor T cells to a second culture medium comprising ascorbate; and
    culturing the progenitor T cells in the second culture medium for a sufficient time to produce differentiated T cells from the progenitor T cells.

2. The method of claim 1, wherein the first culture medium comprises minimal essential medium (MEM) as the basal culture medium.

3. The method of claim 1, wherein the first culture medium comprises Iscove's Modified Dulbecco's Medium (IMDM) as the basal culture medium.

4. The method of claim 1, wherein the second culture medium comprises alpha modification MEM (αMEM) as the basal culture medium.

5. The method of claim 1, wherein the cells modified to express a notch ligand comprise OP9-DL1 cells.

6. The method of claim 1, wherein the cells are cultured in the first culture medium for less than about 30 days.

7. The method of claim 1, wherein the progenitor T cells are cultured in the second culture medium for at least 7 days to produce differentiated T cells from the progenitor T cells.

8. The method of claim 1, wherein the ascorbate is phosphoascorbate.

9. The method of claim 1, wherein the ascorbate is present in an effective amount to preferentially differentiate T cells over NK cells.

10. The method of claim 1, wherein the amount of ascorbate in the second culture medium is from about 10-1000 μg/mL.

11. The method of claim 1, wherein the first culture medium comprises IL-7, Flt3 ligand, or both IL-7 and Flt3 ligand.

12. The method of claim 1, wherein the hematopoietic stem cells, the hematopoietic progenitor cells, or both the hematopoietic stem cells and the hematopoietic progenitor cells express CD34.

13. The method of claim 1, wherein the first culture medium and the second culture medium lack nucleosides.

* * * * *